United States Patent
Miyamoto et al.

(10) Patent No.: US 9,897,028 B2
(45) Date of Patent: Feb. 20, 2018

(54) DIAGNOSIS SYSTEM OF INTERNAL COMBUSTION ENGINE

(71) Applicant: TOYOTA JIDOSHA KABUSHIKI KAISHA, Toyota-shi, Aichi-ken (JP)

(72) Inventors: Hiroshi Miyamoto, Shizuoka (JP); Keiichiro Aoki, Shizuoka (JP); Yasushi Iwazaki, Ebina (JP)

(73) Assignee: TOYOTA JIDOSHA KABUSHIKI KAISHA, Toyota-shi, Aichi (JP)

( * ) Notice: Subject to any disclaimer, the term of this patent is extended or adjusted under 35 U.S.C. 154(b) by 12 days.

(21) Appl. No.: 14/900,849

(22) PCT Filed: Jun. 26, 2013

(86) PCT No.: PCT/JP2013/067529
§ 371 (c)(1),
(2) Date: Dec. 22, 2015

(87) PCT Pub. No.: WO2014/207839
PCT Pub. Date: Dec. 31, 2014

(65) Prior Publication Data
US 2016/0160778 A1 Jun. 9, 2016

(51) Int. Cl.
*F02D 41/14* (2006.01)
*F02D 41/12* (2006.01)
(Continued)

(52) U.S. Cl.
CPC ........... *F02D 41/1495* (2013.01); *F01N 3/10* (2013.01); *F02D 41/126* (2013.01);
(Continued)

(58) Field of Classification Search
CPC ..... F02D 41/1495; F02D 41/1439; F01N 3/10
See application file for complete search history.

(56) References Cited

U.S. PATENT DOCUMENTS 5,956,943 A * 9/1999 Carnevale ........... F02D 41/1474
123/688
2010/0319667 A1* 12/2010 Yoshikawa ......... F02D 41/1495
123/690
(Continued)

FOREIGN PATENT DOCUMENTS

JP 02136538 A * 5/1990 ............ F01N 11/007
JP 2001-242126 A 9/2001
(Continued)

*Primary Examiner* — Patrick Maines
(74) *Attorney, Agent, or Firm* — Andrews Kurth Kenyon LLP

(57) ABSTRACT

An internal combustion engine comprises an exhaust purification catalyst and an air-fuel ratio sensor arranged at a downstream side of the exhaust purification catalyst, stops or decreases a feed of fuel as fuel cut control, and controls an air-fuel ratio of exhaust gas to a rich air-fuel ratio after the end of the fuel cut control as post reset rich control. The diagnosis system calculates a first characteristic of change of air-fuel ratio at the time when the output air-fuel ratio first passes a first air-fuel ratio region leaner than a stoichiometric air-fuel ratio and a second characteristic of change of air-fuel ratio at the time when the output air-fuel ratio first passes a second air-fuel ratio region including a stoichiometric air-fuel ratio. The diagnosis system diagnoses the abnormality of the air-fuel ratio sensor based on the first characteristic of change of air-fuel ratio and the second characteristic of change of air-fuel ratio. As a result, it is possible to suppress the effects of the change of state of the exhaust purification catalyst while accurately diagnosing the abnormality of deterioration of response of a downstream side air-fuel ratio sensor.

13 Claims, 12 Drawing Sheets

(51) Int. Cl.
*F02D 41/22* (2006.01)
*F01N 3/10* (2006.01)
*G01N 27/41* (2006.01)

(52) U.S. Cl.
CPC ..... *F02D 41/1439* (2013.01); *F02D 41/1456* (2013.01); *F02D 41/222* (2013.01); *F01N 3/106* (2013.01); *G01N 27/41* (2013.01)

(56) References Cited

U.S. PATENT DOCUMENTS

| | | | |
|---|---|---|---|
| 2010/0324802 A1* | 12/2010 | Ogiso | F02D 41/1495 701/103 |
| 2011/0077908 A1 | 3/2011 | Odendall | |
| 2011/0106396 A1 | 5/2011 | Moll et al. | |
| 2011/0225951 A1* | 9/2011 | Sato | F02D 41/222 60/274 |
| 2011/0283981 A1* | 11/2011 | Kawamura | F01N 3/101 123/703 |
| 2012/0222474 A1 | 9/2012 | Plonka et al. | |
| 2012/0324869 A1 | 12/2012 | Nakamura | |
| 2016/0069242 A1* | 3/2016 | Miyamoto | F01N 11/00 60/277 |

FOREIGN PATENT DOCUMENTS

| | | | | |
|---|---|---|---|---|
| JP | 2004-225684 A | | 8/2004 | |
| JP | 2004225684 A | * | 8/2004 | |
| JP | 2005-030358 A | | 2/2005 | |
| JP | 2007-192093 A | | 8/2007 | |
| JP | 2008169776 A | * | 7/2008 | .......... G01M 15/042 |
| JP | 2010-007534 A | | 1/2010 | |
| JP | 2010-025090 A | | 2/2010 | |
| JP | 2010-163904 A | | 7/2010 | |
| JP | 2011-106415 A | | 6/2011 | |
| JP | 2011-196230 A | | 10/2011 | |
| JP | 2011-208605 A | | 10/2011 | |
| JP | 2012-052462 A | | 3/2012 | |
| JP | 2012-127356 A | | 7/2012 | |

* cited by examiner

DIAGNOSIS SYSTEM OF INTERNAL COMBUSTION ENGINE

CROSS-REFERENCE TO RELATED APPLICATION

This is a national phase application based on the PCT International Patent Application No. PCT/JP2013/067529 filed Jun. 26, 2013, the entire contents of which are incorporated herein by reference.

TECHNICAL FIELD

The present invention relates to a diagnosis system of an internal combustion engine.

BACKGROUND ART

Known in the past has been an internal combustion engine providing an air-fuel ratio sensor in an exhaust passage of the internal combustion engine and controlling an amount of fuel which is fed to the internal combustion engine based on an output of the air-fuel ratio sensor.

The air-fuel ratio sensor used in such an internal combustion engine gradually deteriorates along with use. As such deterioration, for example, deterioration of response of the air-fuel ratio sensor may be mentioned. The deterioration of response of the air-fuel ratio sensor occurs due to air holes provided in a sensor cover for preventing a sensor element from being covered by water ending up being partially clogged by particulate matter (PM). If the air holes are partially clogged in this way, the exchange of gas between the inside and outside of the sensor cover becomes slower, and as a result the output of the air-fuel ratio sensor ends up becoming blunter. If such deterioration of the air-fuel ratio sensor occurs, the various control operations performed by the control system of an internal combustion engine end up being hindered.

Therefore, diagnosis systems diagnosing deterioration of air-fuel ratio sensors have been proposed (for example, see PLTs 1 to 5). As such a diagnosis system, for example, one making a target air-fuel ratio change in a step manner and along with this detecting a first response time until an output value of the air-fuel ratio sensor reaches a first predetermined value and a second response time larger than the first predetermined value and using the two times of the first response time and the second response time as the basis to judge deterioration of the air-fuel ratio sensor has been proposed (for example, PLT 1). Here, as patterns of deterioration of an air-fuel ratio sensor, there is deterioration of response where the response time becomes slower and deterioration of gain where the response itself increases or decreases. As opposed to this, according to the diagnosis system described in PLT 1, by using the first response time and the second response time as the basis to judge deterioration of an air-fuel ratio sensor, it is considered possible to accurately identify by which of the two patterns of deterioration the deterioration of the air-fuel ratio sensor is being caused.

CITATIONS LIST

Patent Literature

PLT 1: Japanese Patent Publication No. 2007-192093A
PLT 2: Japanese Patent Publication No. 2004-225684A
PLT 3: Japanese Patent Publication No. 2001-242126A
PLT 4: Japanese Patent Publication No. 2010-007534A
PLT 5: Japanese Patent Publication No. 2011-106415A

SUMMARY OF INVENTION

Technical Problem

In this regard, deterioration of response of an air-fuel ratio sensor is diagnosed by making the air-fuel ratio of the exhaust gas flowing out from the internal combustion engine change in steps and detecting the response of the air-fuel ratio sensor with respect to this step like change. Further, the greater the extent by which the air-fuel ratio of the exhaust gas discharged from the internal combustion engine is made to change in steps, the higher the precision of diagnosis of the deterioration of response.

Here, when performing fuel cut control stopping or greatly decreasing the feed of fuel to the combustion chambers, the air-fuel ratio of the exhaust gas flowing out from the exhaust purification catalyst becomes leaner than the stoichiometric air-fuel ratio. The lean degree becomes extremely large. Therefore, right after the start of fuel cut control or right after the end of fuel cut control, the air-fuel ratio of the exhaust gas exhausted from the internal combustion engine is made to greatly change in steps. For this reason, right after the start of fuel cut control or right after the end of fuel cut control, high precision diagnosis of deterioration of response is possible.

On the other hand, in an internal combustion engine controlling a fuel amount based on the output of an air-fuel ratio sensor, an air-fuel ratio sensor is often provided at the downstream side of the exhaust purification catalyst as well. In such a case, the exhaust gas discharged from the internal combustion engine passes through the exhaust purification catalyst then reaches the downstream side air-fuel ratio sensor. For this reason, when the exhaust purification catalyst has an oxygen storage ability, the air-fuel ratio of the exhaust gas reaching the downstream side air-fuel ratio sensor changes in accordance with not only the exhaust gas discharged from the internal combustion engine, but also the oxygen storage ability, oxygen storage amount, etc. of the exhaust purification catalyst.

For this reason, when, as mentioned above, making the air-fuel ratio of the exhaust gas discharged from the internal combustion engine greatly change in a step like manner so as to diagnose deterioration of response, sometimes the output of the downstream side air-fuel ratio sensor ends up changing in accordance with the state of the exhaust purification catalyst. In such a case, even if the actual response of the downstream side air-fuel ratio sensor is constant, if the state of the exhaust purification catalyst changes, along with this, the output of the downstream side air-fuel ratio sensor will end up changing.

As opposed to this, for example, if diagnosing deterioration of response right after the end of fuel cut control, it is possible to perform the diagnosis in a state grasping the oxygen storage amount in the exhaust purification catalyst. For this reason, it is possible to reduce the effect of the state of the exhaust purification catalyst on the output of the downstream side air-fuel ratio sensor and, as a result, raise the precision of diagnosis of deterioration of response of the downstream side air-fuel ratio sensor.

However, even if diagnosing deterioration of response right after the end of fuel cut control in this way, the output of the downstream side air-fuel ratio sensor still changes according to the state of the exhaust purification catalyst. Further, if the output of the downstream side air-fuel ratio sensor changes according to the state of the exhaust purification catalyst in this way, it ends up no longer possible to accurately diagnose deterioration of response of the downstream side air-fuel ratio sensor.

Therefore, in view of the above problems, an object of the present invention is to provide a diagnosis system of an internal combustion engine able to suppress the effects of the change of state of the exhaust purification catalyst while accurately diagnosing the abnormality of deterioration of response of a downstream side air-fuel ratio sensor.

Solution to Problem

In order to solve the above problem, in a first invention, there is provided a diagnosis system of an internal combustion engine comprising an exhaust purification catalyst arranged in an exhaust passage of the internal combustion engine and being able to store oxygen in inflowing exhaust gas and an air-fuel ratio sensor arranged at a downstream side of the exhaust purification catalyst in a direction of exhaust flow and detecting an air-fuel ratio of exhaust gas flowing out from the exhaust purification catalyst, stopping or decreasing a feed of fuel to a combustion chamber as fuel cut control, and controlling an air-fuel ratio of exhaust gas flowing into the exhaust purification catalyst after the end of the fuel cut control to a rich air-fuel ratio richer than a stoichiometric air-fuel ratio as post reset rich control, wherein the diagnosis system comprises a first change characteristic calculating means for calculating a first characteristic of change of air-fuel ratio when the output air-fuel ratio of the air-fuel ratio sensor first passes a first air-fuel ratio region which is a part of an air-fuel ratio region of a stoichiometric air-fuel ratio or more, after an end of the fuel cut control, based on an output air-fuel ratio output from the air-fuel ratio sensor, a second change characteristic calculating means for calculating a second characteristic of change of air-fuel ratio when the output air-fuel ratio of the air-fuel ratio sensor first passes a second air-fuel ratio region including the stoichiometric air-fuel ratio and different from the first air-fuel ratio region, after the end of the fuel cut control, based on an output air-fuel ratio output from the air-fuel ratio sensor, and an abnormality diagnosing means for diagnosing abnormality of the air-fuel ratio sensor based on the first characteristic of change calculated by the first change characteristic calculating means and the second characteristic of change calculated by the second change characteristic calculating means.

In a second invention, the abnormality diagnosing means corrects the first characteristic of change of air-fuel ratio based on the second characteristic of change of air-fuel ratio to calculate a corrected characteristic of change of air-fuel ratio and diagnoses abnormality of the air-fuel ratio sensor based on the corrected characteristic of change of air-fuel ratio in the first invention.

In a third invention, the first characteristic of change of air-fuel ratio is a first change of speed of air-fuel ratio which is a speed of change when the output air-fuel ratio of the air-fuel ratio sensor first passes through the first air-fuel ratio region, and the abnormality diagnosing means judges that the air-fuel ratio sensor is abnormal when a corrected change of speed of air-fuel ratio calculated by correcting the first change of speed of air-fuel ratio based on the second characteristic of change of air-fuel ratio is slower than a speed of change used as reference for abnormality, and judges that the air-fuel ratio sensor is normal when the corrected change of speed of air-fuel ratio is faster than the speed of change used as reference for abnormality in the second invention.

In a forth invention, the second characteristic of change of air-fuel ratio is a second change of speed of air-fuel ratio which is a speed of change at the time when an output air-fuel ratio of the air-fuel ratio sensor first passes through the second air-fuel ratio region, and the abnormality diagnosing means, in calculating the corrected change of speed of air-fuel ratio, corrects the first change of speed of air-fuel ratio so that the faster the second change of speed of air-fuel ratio, the slower the corrected change of speed of air-fuel ratio becomes in the third invention.

In a fifth invention, first characteristic of change of air-fuel ratio is a first cumulative value of air-fuel ratio obtained by cumulatively adding the output air-fuel ratio of the air-fuel ratio sensor when the output air-fuel ratio is in the first air-fuel ratio region, and the abnormality diagnosing means judges that the air-fuel ratio sensor is abnormal when a corrected cumulative value of air-fuel ratio calculated by correcting the first cumulative value of air-fuel ratio based on the second characteristic of change of air-fuel ratio is a cumulative value used as reference for abnormality or more and judges that the air-fuel ratio sensor is normal when the corrected cumulative value of air-fuel ratio is smaller than the cumulative value used as reference for abnormality in the second invention.

In a sixth invention, the second characteristic of change of air-fuel ratio is a speed of change when an output air-fuel ratio of the air-fuel ratio sensor first passes through the second air-fuel ratio region, defined as a second change of speed of air-fuel ratio, and the abnormality diagnosing means, in calculating the corrected cumulative value of air-fuel ratio, corrects the first cumulative value of air-fuel ratio so that the faster the second change of speed of air-fuel ratio, the slower the corrected cumulative value of air-fuel ratio becomes in the fifth invention.

In a seventh invention, the second air-fuel ratio region is a region between a second region upper limit air-fuel ratio leaner than the stoichiometric air-fuel ratio and a second region lower limit air-fuel ratio at a rich side from the stoichiometric air-fuel ratio in the fourth or sixth invention.

In an eighth invention, the abnormality diagnosing means does not correct the first change of speed of air-fuel ratio or cumulative value of air-fuel ratio based on the second change of speed of air-fuel ratio when a predetermined time or more elapses from when an output air-fuel ratio of the air-fuel ratio sensor enters the second air-fuel ratio region in the seventh invention.

In a ninth invention, the air-fuel ratio sensor is a limit current type air-fuel ratio sensor outputting a limit current when an air-fuel ratio of exhaust gas passing through the air-fuel ratio sensor is within a predetermined air-fuel ratio region, and the first air-fuel ratio region and the second air-fuel ratio region are within the predetermined air-fuel ratio region where the air-fuel ratio sensor generates a limit current in any one of the first to eighth inventions.

In a tenth invention, the first air-fuel ratio region is a region between the first region upper limit air-fuel ratio and a first region lower limit air-fuel ratio at a rich side from the first region upper limit air-fuel ratio, the second air-fuel ratio region is a region between the second region upper limit air-fuel ratio and a second region lower limit air-fuel ratio at a rich side from the second region upper limit air-fuel ratio, and the second region upper limit air-fuel ratio is the first region lower limit air-fuel ratio or less in any one of the first to ninth inventions.

In a eleventh invention, the second characteristic of change of air-fuel ratio is a second change of speed of air-fuel ratio which is a change of speed when an output air-fuel ratio of the air-fuel ratio sensor first passes through the second air-fuel ratio region, and the abnormality diagnosing means judges that the exhaust purification catalyst is deteriorating when it is judged that the second change of speed of air-fuel ratio is faster than a speed of change of judgment of abnormality of catalyst in any one of the first to tenth inventions.

In order to solve the above problem, in a twelfth invention, there is provided a diagnosis system of an internal combustion engine comprising an exhaust purification catalyst arranged in an exhaust passage of the internal combustion engine and able to store oxygen in inflowing exhaust gas and an air-fuel ratio sensor arranged at a downstream side of the exhaust purification catalyst in a direction of exhaust flow and detecting an air-fuel ratio of exhaust gas flowing out from the exhaust purification catalyst, stopping or decreasing a feed of fuel to a combustion chamber as fuel cut control, and controlling an air-fuel ratio of exhaust gas flowing into the exhaust purification catalyst after the end of the fuel cut control to a rich air-fuel ratio richer than a stoichiometric air-fuel ratio as post reset rich control, wherein the diagnosis system comprises a change characteristic calculating means for calculating a characteristic of change of air-fuel ratio at the time when the output air-fuel ratio of the air-fuel ratio sensor first passes a part of an air-fuel ratio region of a stoichiometric air-fuel ratio or more, after the end of the fuel cut control, based on an output air-fuel ratio output from the air-fuel ratio sensor, a converged air-fuel ratio detecting means for detecting an output air-fuel ratio when a speed of change of output air-fuel ratio of the air-fuel ratio sensor becomes a reference speed or less after the end of the fuel cut control, as a converged output air-fuel ratio, based on an output air-fuel ratio output from the air-fuel ratio sensor, and an abnormality diagnosing means for diagnosing abnormality of the air-fuel ratio sensor base on the characteristic of change of air-fuel ratio calculated by the change characteristic calculating means and a converged output air-fuel ratio detected by the converged air-fuel ratio detecting means.

In a thirteenth invention, the abnormality diagnosing means corrects the characteristic of change of air-fuel ratio to calculate a corrected characteristic of change of air-fuel ratio and diagnoses abnormality of the air-fuel ratio sensor based on the corrected characteristic of change of air-fuel ratio if the converged output air-fuel ratio detected by the converged air-fuel ratio detecting means is a rich air-fuel ratio in the twelfth invention.

In a fourteenth invention, the characteristic of change of air-fuel ratio is a change of speed of air-fuel ratio which is a change of speed when an output air-fuel ratio of the air-fuel ratio sensor first passes through the air-fuel ratio region, and the abnormality diagnosing means judges that the air-fuel ratio sensor is abnormal when a corrected change of speed of air-fuel ratio calculated by correcting the change of speed of air-fuel ratio is slower than a speed of change used as reference for abnormality, and judges that the air-fuel ratio sensor is normal when the corrected change of speed of air-fuel ratio is faster than a speed of change used as reference for abnormality in the thirteenth invention.

In a fifteenth invention, the characteristic of change of air-fuel ratio is a cumulative value of air-fuel ratio obtained by cumulatively adding an output air-fuel ratio of the air-fuel ratio sensor when the output air-fuel ratio is in the air-fuel ratio region, the abnormality diagnosing means judges that the air-fuel ratio sensor is abnormal when a corrected cumulative value of air-fuel ratio calculated by correcting the cumulative value of air-fuel ratio is a cumulative value used as reference for abnormality or more, and judges that the air-fuel ratio sensor is normal when the corrected cumulative value of air-fuel ratio is smaller than the cumulative value used as reference for abnormality in the thirteenth invention.

In a sixteenth invention, the post reset rich control is made to end when an output air-fuel ratio of the air-fuel ratio sensor becomes an end judgment air-fuel ratio richer than the stoichiometric air-fuel ratio or less than the end judgment air-fuel ratio, and when the converged air-fuel ratio detecting means detects a converged output air-fuel ratio, after the end of the fuel cut control, until a speed of change of an output air-fuel ratio of the air-fuel ratio sensor becomes a reference speed, the post reset rich control is continued even if an output air-fuel ratio of the air-fuel ratio sensor reaches the end judgment air-fuel ratio in any one of the twelfth to fifteenth inventions.

In a seventeenth invention, when judgment by the abnormality diagnosing means is not performed, the converged air-fuel ratio detecting means does not detect a converged output air-fuel ratio and after the end of the fuel cut control, even if a speed of change of an output air-fuel ratio of the air-fuel ratio sensor does not become a reference speed, the post reset rich control is made to end if an output air-fuel ratio of the air-fuel ratio sensor reaches the end judgment air-fuel ratio in the sixteenth invention.

In order to solve the above problem, in an eighteenth invention, there is provided a diagnosis system of an internal combustion engine comprising an exhaust purification catalyst arranged in an exhaust passage of the internal combustion engine and able to store oxygen in inflowing exhaust gas and an air-fuel ratio sensor arranged at a downstream side of the exhaust purification catalyst in a direction of exhaust flow and detecting an air-fuel ratio of exhaust gas flowing out from the exhaust purification catalyst, stopping or decreasing a feed of fuel to a combustion chamber as fuel cut control, and controlling an air-fuel ratio of exhaust gas flowing into the exhaust purification catalyst after the end of the fuel cut control to a rich air-fuel ratio richer than a stoichiometric air-fuel ratio as post reset rich control, wherein the diagnosis system comprises a first change speed calculating means for calculating a first change of speed of air-fuel ratio which is a change of speed at the time when the output air-fuel ratio of the air-fuel ratio sensor first passes a first air-fuel ratio region which is a part of an air-fuel ratio region of a stoichiometric air-fuel ratio or more, after an end of the fuel cut control, based on an output air-fuel ratio output from the air-fuel ratio sensor, a second change speed calculating means for calculating a second change of speed of air-fuel ratio which is a change of speed when the output air-fuel ratio of the air-fuel ratio sensor first passes a second air-fuel ratio region different from the first air-fuel ratio region, based on an output air-fuel ratio output from the air-fuel ratio sensor, and an abnormality diagnosing means for diagnosing abnormality of the air-fuel ratio sensor based on a corrected change of speed of air-fuel ratio calculated by correcting the first change of speed of air-fuel ratio calculated by the first change speed calculating means based on the second change of speed of air-fuel ratio calculated by the second change speed calculating means, wherein the abnormality diagnosing means corrects the first change of speed of air-fuel ratio so that the corrected change of speed of air-fuel ratio becomes slower the faster the second change of speed of air-fuel ratio, judges that the air-fuel ratio sensor is abnormal when the corrected change of speed of air-fuel ratio is slower than a speed of change used as reference for abnormality, and judges that the air-fuel ratio sensor is normal when the first change of speed of air-fuel ratio corrected based on the second change of speed of air-fuel ratio is faster than a speed of change used as reference for abnormality.

In a nineteenth invention, in diagnosing abnormality of the air-fuel ratio sensor, when it is judged that the air-fuel ratio sensor is abnormal, a warning light is lit in any one of the first to eighteenth inventions.

Advantageous Effects of Invention

According to the present invention, there is provided a diagnosis system of an internal combustion engine able to suppress the effects of the change of state of the exhaust purification catalyst while accurately diagnosing the abnormality of deterioration of response of a downstream side air-fuel ratio sensor.

DESCRIPTION OF EMBODIMENTS

Figure 1:
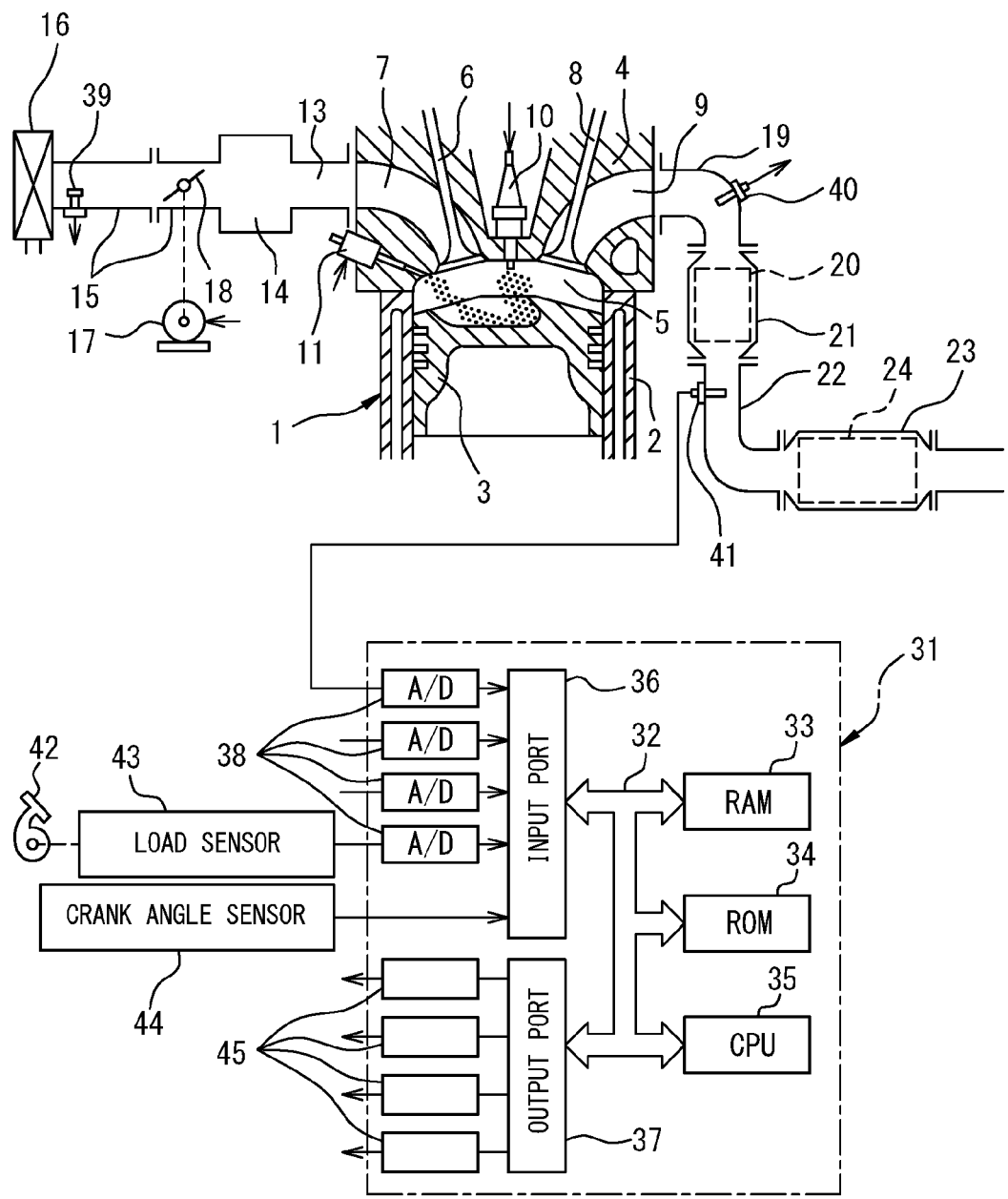
FIG. 1 is a view schematically showing an internal combustion engine in which the diagnosis system of the present invention is used.

Referring to the drawings, a diagnosis system of an internal combustion engine of the present invention will be explained in detail below. Note that, in the following explanation, similar component elements are assigned the same reference numerals. FIG. 1 is a view which schematically shows an internal combustion engine in which a control system according to a first embodiment of the present invention is used.

<Explanation of Internal Combustion Engine as a Whole>

Referring to FIG. 1, 1 indicates an engine body, 2 a cylinder block, 3 a piston which reciprocates inside the cylinder block 2, 4 a cylinder head which is fastened to the cylinder block 2, 5 a combustion chamber which is formed between the piston 3 and the cylinder head 4, 6 an intake valve, 7 an intake port, 8 an exhaust valve, and 9 an exhaust port. The intake valve 6 opens and closes the intake port 7, while the exhaust valve 8 opens and closes the exhaust port 9.

As shown in FIG. 1, at the center part of the inside wall surface of the cylinder head 4, a spark plug 10 is arranged. A fuel injector 11 is arranged around the inside wall surface of the cylinder head 4. The spark plug 10 is configured to cause generation of a spark in accordance with an ignition signal. Further, the fuel injector 11 injects a predetermined amount of fuel into the combustion chamber 5 in accordance with an injection signal. Note that, the fuel injector 11 may be arranged so as to inject fuel inside the intake port 7. Further, in the present embodiment, as the fuel, gasoline with a stoichiometric air-fuel ratio of 14.6 is used. However, in the internal combustion engine in which the diagnosis system of the present invention is used, another fuel may also be used.

The intake port 7 in each cylinder is connected through a corresponding intake runner 13 to a surge tank 14. The surge tank 14 is connected through an intake pipe 15 to an air cleaner 16. The intake port 7, intake runner 13, surge tank 14, and intake pipe 15 form an intake passage. Further, inside the intake pipe 15, a throttle valve 18 which is driven by a throttle valve drive actuator 17 is arranged. The throttle valve 18 can be turned by the throttle valve drive actuator 17 to thereby change the opening area of the intake passage.

On the other hand, the exhaust port 9 in each cylinder is connected to an exhaust manifold 19. The exhaust manifold 19 has a plurality of runners which are connected to the exhaust ports 9 and a header at which these runners are collected. The header of the exhaust manifold 19 is connected to an upstream side casing 21 which has an upstream side exhaust purification catalyst 20 built into it. The upstream side casing 21 is connected through an exhaust pipe 22 to a downstream side casing 23 which has a downstream side exhaust purification catalyst 24 built into it. The exhaust port 9, exhaust manifold 19, upstream side casing 21, exhaust pipe 22, and downstream side casing 23 form an exhaust passage.

The electronic control unit (ECU) 31 is comprised of a digital computer provided with components which are connected together through a bidirectional bus 32 such as a RAM (random access memory) 33, ROM (read only memory) 34, CPU (microprocessor) 35, input port 36, and output port 37. In the intake pipe 15, an air flow meter 39 is arranged for detecting the flow rate of air which flows through the intake pipe 15. The output of this air flow meter 39 is input through a corresponding AD converter 38 to the input port 36. Further, at the header of the exhaust manifold 19, an upstream side air-fuel ratio sensor 40 is arranged which detects the air-fuel ratio of the exhaust gas which flows through the inside of the exhaust manifold 19 (that is, the exhaust gas which flows into the upstream side exhaust purification catalyst 20). In addition, in the exhaust pipe 22, a downstream side air-fuel ratio sensor 41 is arranged which detects the air-fuel ratio of the exhaust gas flowing through the inside of the exhaust pipe 22 (that is, the exhaust gas which flows out from the upstream side exhaust purification catalyst 20 and flows into the downstream side exhaust purification catalyst 24). The outputs of these air-fuel ratio sensors 40 and 41 are also input through the corresponding AD converters 38 to the input port 36. Note that, the configurations of these air-fuel ratio sensors 40 and 41 will be explained later.

Further, an accelerator pedal 42 has a load sensor 43 connected to it which generates an output voltage which is proportional to the amount of depression of the accelerator pedal 42. The output voltage of the load sensor 43 is input to the input port 36 through a corresponding AD converter 38. The crank angle sensor 44 generates an output pulse every time, for example, a crankshaft rotates by 15 degrees. This output pulse is input to the input port 36. The CPU 35 calculates the engine speed from the output pulse of this crank angle sensor 44. On the other hand, the output port 37 is connected through corresponding drive circuits 45 to the spark plugs 10, fuel injectors 11, and throttle valve drive actuator 17.

<Explanation of Exhaust Purification Catalyst>

The upstream side exhaust purification catalyst 20 and downstream side exhaust purification catalyst 24 both have similar configurations. Below, only the upstream side exhaust purification catalyst 20 will be explained, but the downstream side exhaust purification catalyst 24 also has a similar configuration and actions.

The upstream side exhaust purification catalyst 20 is a three-way catalyst having an oxygen storage ability. Specifically, the upstream side exhaust purification catalyst 20 is comprised of a carrier made of ceramic on which a precious metal having a catalytic action (for example, platinum (Pt)) and a substance having an oxygen storage ability (for example, ceria ($CeO_2$)) are carried. The upstream side exhaust purification catalyst 20 has oxygen storage ability in addition to a catalytic action simultaneously removing the unburned gas (HC, CO, etc.) and nitrogen oxides ($NO_X$) if reaching a predetermined activation temperature.

According to the oxygen storage ability of the upstream side exhaust purification catalyst 20, the upstream side exhaust purification catalyst 20 stores the oxygen in the exhaust gas when the air-fuel ratio of the exhaust gas flowing into the upstream side exhaust purification catalyst 20 is leaner than the stoichiometric air-fuel ratio (below referred to as the "lean air-fuel ratio"). On the other hand, the upstream side exhaust purification catalyst 20 releases the oxygen stored in the upstream side exhaust purification catalyst 20 when the air-fuel ratio of the inflowing exhaust gas is richer than the stoichiometric air-fuel ratio (below, referred to as the "rich air-fuel ratio"). Note that, the "air-fuel ratio of the exhaust gas" means the ratio of the mass of the fuel to the mass of the air supplied until the exhaust gas is generated. Usually, it means the ratio of the mass of the fuel to the mass of the air fed into a combustion chamber 5. In this Description, sometimes the air-fuel ratio of the exhaust gas will be referred to as the "exhaust air-fuel ratio".

The upstream side exhaust purification catalyst 20 has a catalyzing action and an oxygen storage ability and therefore has an action of removing $NO_X$ and unburned gas in accordance with the oxygen storage amount. If the air-fuel ratio of the exhaust gas flowing into the upstream side exhaust purification catalyst 20 is a lean air-fuel ratio, when the oxygen storage amount is small, the upstream side exhaust purification catalyst 20 will store the oxygen in the exhaust gas and along with this the $NO_X$ will be reduced. However, there are limits to the oxygen storage ability. If the oxygen storage amount of the upstream side exhaust purification catalyst 20 exceeds the upper limit storage amount, the upstream side exhaust purification catalyst 20 will no longer store almost any further oxygen. In this case, if the air-fuel ratio of the exhaust gas flowing into the upstream side exhaust purification catalyst 20 is the lean air-fuel ratio, air-fuel ratio of the exhaust gas flowing out from the upstream side exhaust purification catalyst 20 will also become the lean air-fuel ratio.

On the other hand, if the air-fuel ratio of the exhaust gas flowing into the upstream side exhaust purification catalyst 20 is a rich air-fuel ratio, when the oxygen storage amount is large, the oxygen stored in the upstream side exhaust purification catalyst 20 will be released and the unburned gas in the exhaust gas will be removed by oxidation. However, if the oxygen storage amount of the upstream side exhaust purification catalyst 20 becomes smaller and falls below the lower limit storage amount, the upstream side exhaust purification catalyst 20 will no longer release almost any further oxygen. In this case, if the air-fuel ratio of the exhaust gas flowing into the upstream side exhaust purification catalyst 20 is the rich air-fuel ratio, the air-fuel ratio of the exhaust gas flowing out from the upstream side exhaust purification catalyst 20 will also become a rich air-fuel ratio.

As explained above, according to the exhaust purification catalysts 20, 24 used in the present embodiment, the property of removal of the $NO_X$ and unburned gas in the exhaust gas changes in accordance with the air-fuel ratio of the exhaust gas flowing into the exhaust purification catalyst and the oxygen storage amount. Note that, the exhaust purification catalysts 20, 24 may also be catalysts different from three-way catalysts, as long as they have a catalytic action and oxygen storage ability.

<Explanation of Air-Fuel Ratio Sensor>

Figure 2:
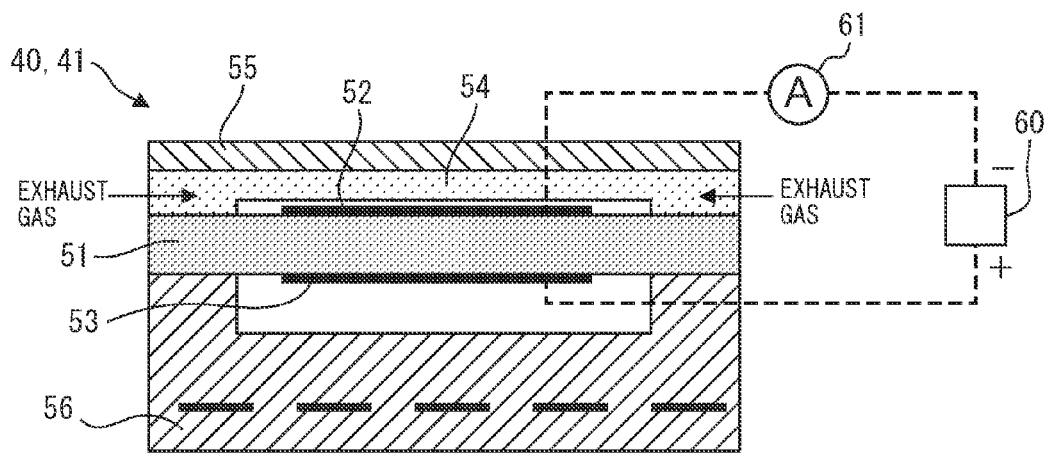
FIG. 2 is a schematic cross-sectional view of an air-fuel ratio sensor.

In the present embodiment, as the air-fuel ratio sensors 40, 41, limit current type air-fuel ratio sensors are used. FIG. 2 will be used to simply explain the structures of the air-fuel ratio sensors 40, 41. The air-fuel ratio sensors 40, 41 are provided with solid electrolyte layers 51, exhaust side electrodes 52 arranged on one side face of the same, atmosphere side electrodes 53 arranged on the other side face of the same, diffusion regulating layers 54 regulating diffusion of the passing exhaust gas, protective layers 55 protecting the diffusion regulating layers 54, and heater parts 56 heating the air-fuel ratio sensors 40, 41.

Each solid electrolyte layer 51 is formed from a sintered body of an oxygen ion conductive oxide such as $ZrO_2$ (zirconia), $HfO_2$, $ThO_2$, $Bi_2O_3$, etc. in which CaO, MgO, $Y_2O_3$, $Yb_2O_3$, etc. is added as a stabilizer. Further, the diffusion regulating layer 54 is formed from a porous sintered body of alumina, magnesia, silica, spinel, mullite, or other heat resistant inorganic substance. Further, the exhaust side electrode 52 and the atmosphere side electrode 53 are formed by platinum or another precious metal with a high catalytic activity.

Further, between the exhaust side electrode and the atmosphere side electrode, a voltage applying device 60 mounted in the ECU 31 is used to apply the sensor applied voltage V. In addition, the ECU 31 is provided with a current detection device 61 detecting the current I flowing between these electrodes 52, 53 through the solid electrolyte layer when applying the sensor applied voltage. The current detected by this current detection device 61 is the output current of the air-fuel ratio sensors 40, 41.

Figure 3:
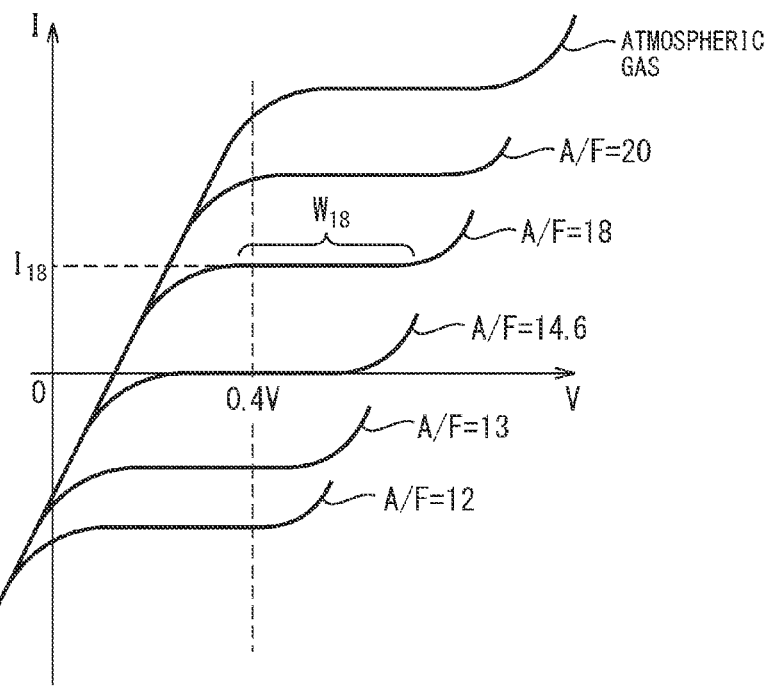
FIG. 3 is a view showing a relationship between a sensor applied voltage and output current at different exhaust air-fuel ratios.

The thus configured air-fuel ratio sensors 40, 41 have voltage-current (V-I) characteristics such as shown in FIG. 3. As will be understood from FIG. 3, the output current (I) becomes larger the larger (the leaner) the exhaust air-fuel ratio. Further, the line V-I at each exhaust air-fuel ratio has a region parallel to the V axis, that is, a region where even if the sensor applied voltage changes, the output current will not change much at all. This voltage region is called the "limit current region". The current at this time is called the "limit current". In FIG. 3, the limit current region and the limit current when the exhaust air-fuel ratio is 18 are respectively shown by $W_{18}$ and $I_{18}$.

On the other hand, in the region where the sensor applied voltage is lower than the limit current region, the output current changes substantially proportionally to the sensor applied voltage. Such a region is called a "proportional region". The slope at this time is determined by the DC element resistance of the solid electrolyte layer 51. Further, in the region where the sensor applied voltage is higher than the limit current region, the output current also increases along with an increase in the sensor applied voltage. In this region, on the exhaust side electrode 52, the moisture included in the exhaust gas breaks down etc. whereby the output voltage changes according to the change in the sensor applied voltage.

Figure 4:
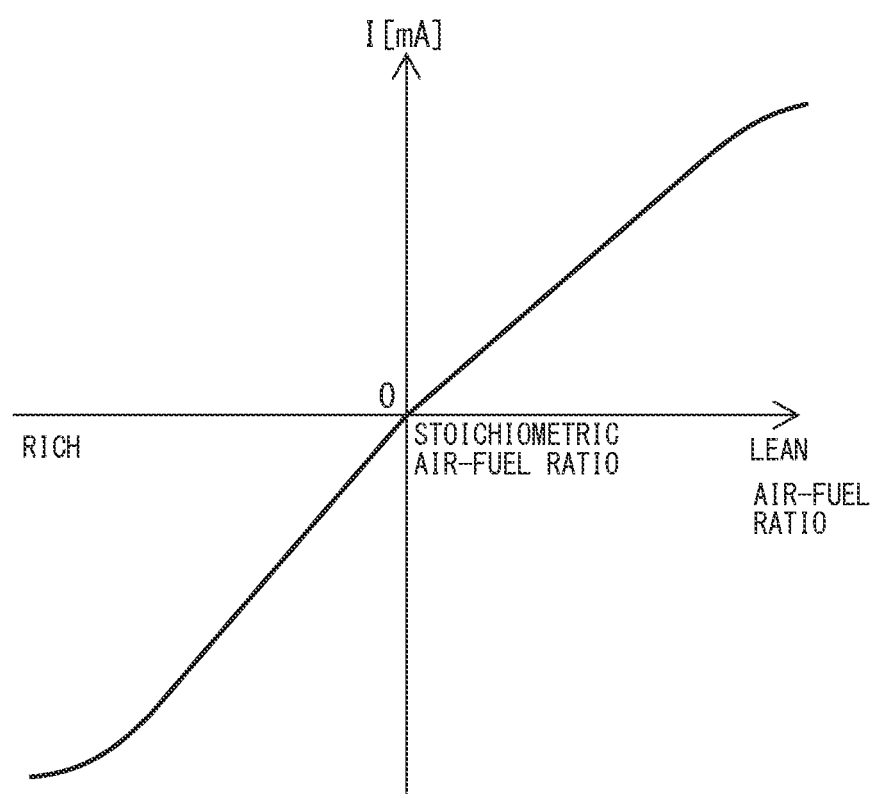
FIG. 4 is a view showing a relationship between an exhaust air-fuel ratio and output current I when making the sensor applied voltage constant.

FIG. 4 is a view showing a relationship between an exhaust air-fuel ratio and output current I when making the applied voltage a constant 0.4V or so. As will be understood from FIG. 4, at the air-fuel ratio sensors 40, 41, the larger the exhaust air-fuel ratio becomes (that is, the leaner), the larger the output current I from the air-fuel ratio sensors 40, 41. In addition, the air-fuel ratio sensors 40, 41 are configured so that when the exhaust air-fuel ratio is the stoichiometric air-fuel ratio, the output current I becomes zero. Further, when the exhaust air-fuel ratio becomes larger than a certain amount or more (in the present embodiment, 18 or more) or when it is smaller than a certain amount or less, the ratio of change of the output current to the change of the exhaust air-fuel ratio becomes smaller.

Note that, in the above example, limit current type air-fuel ratio sensors of the structure shown in FIG. 2 are used as the air-fuel ratio sensors 40, 41. However, so long as the output value changes smoothly with respect to a change in the exhaust air-fuel ratio at least near the stoichiometric air-fuel ratio, another structure of a limit current type air-fuel ratio sensor or an air-fuel ratio sensor not of the limit current type or any other air-fuel ratio sensor may be used.

<Basic Control>

In the thus configured internal combustion engine, based on the outputs of the upstream side air-fuel ratio sensor 40 and the downstream side air-fuel ratio sensor 41, the fuel injection amount from a fuel injector 11 etc. is set so that the air-fuel ratio of the exhaust gas flowing into the upstream side exhaust purification catalyst 20 becomes the optimum target air-fuel ratio based on the engine operating condition. As such a method of setting the fuel injection amount, the method of using the output of the upstream side air-fuel ratio sensor 40 as the basis for controlling the air-fuel ratio of the exhaust gas flowing into the upstream side exhaust purification catalyst 20 so as to become the target air-fuel ratio and using the output of the downstream side air-fuel ratio sensor 41 as the basis for correcting the output of the upstream side air-fuel ratio sensor 40 or changing the target air-fuel ratio may be mentioned.

Further, in the internal combustion engine according to an embodiment of the present invention, at the time of deceleration of the vehicle mounting the internal combustion engine etc., the fuel injection from a fuel injector 11 is stopped or greatly decreased to stop or greatly decrease the supply of fuel to the inside of a combustion chamber 5 as "fuel cut control". This fuel cut control is, for example, performed when the amount of depression of the accelerator pedal 42 is zero or substantially zero (that is, the engine load is zero or substantially zero) and the engine speed is a predetermined speed higher than the speed at the time of idling or is higher than the predetermined speed.

When fuel cut control is performed, air or exhaust gas like air is exhausted from the internal combustion engine, and therefore gas with an extremely high air-fuel ratio (that is, extremely high lean degree) flows into the upstream side exhaust purification catalyst 20. As a result, during fuel cut control, a large amount of oxygen flows into the upstream side exhaust purification catalyst 20, and the oxygen storage amount of the upstream side exhaust purification catalyst 20 reaches the upper limit storage amount.

Further, in the internal combustion engine of the present embodiment, during fuel cut control, oxygen stored in the upstream side exhaust purification catalyst 20 is made to be released by making the air-fuel ratio of the exhaust gas flowing into the upstream side exhaust purification catalyst 20 the rich air-fuel ratio right after the end of the fuel cut control as "post reset rich control". This state is shown in FIG. 5.

Figure 5:
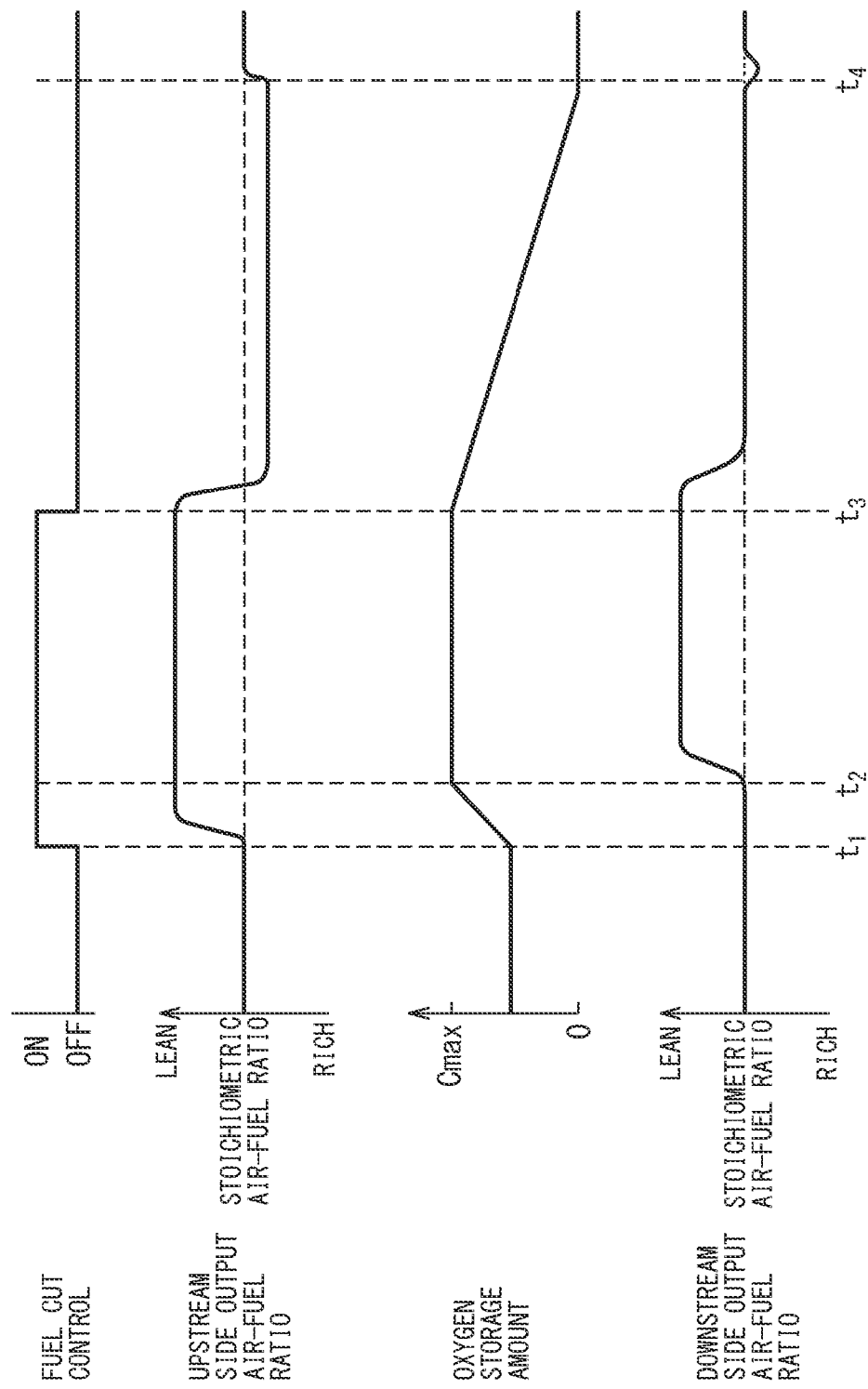
FIG. 5 is a time chart of an upstream side output air-fuel ratio, downstream side output air-fuel ratio, etc. before and after fuel cut control.

FIG. 5 is a time chart of the air-fuel ratio corresponding to the output value of the upstream side air-fuel ratio sensor 40 (below, referred to as the "upstream side output air-fuel ratio"), the oxygen storage amount of the upstream side exhaust purification catalyst 20, and the air-fuel ratio corresponding to the output value of the downstream side air-fuel ratio sensor 41 (below, referred to as the "downstream side output air-fuel ratio") when performing fuel cut control. In the illustrated example, the fuel cut control is started at the time $t_1$ and the fuel cut control is ended at the time $t_3$.

In the illustrated example, if fuel cut control is made to start at the time $t_1$, lean air-fuel ratio exhaust gas is discharged from the engine body 1. Along with this, the output air-fuel ratio of the upstream side air-fuel ratio sensor 40 increases. At this time, the oxygen in the exhaust gas flowing into the upstream side exhaust purification catalyst 20 is stored in the upstream side exhaust purification catalyst 20, and therefore the oxygen storage amount of the upstream side exhaust purification catalyst 20 increases, while the output air-fuel ratio of the downstream side air-fuel ratio sensor 41 remains as the stoichiometric air-fuel ratio.

After that, when, at the time $t_2$, the oxygen storage amount of the upstream side exhaust purification catalyst 20 reaches the upper limit storage amount (Cmax), the upstream side exhaust purification catalyst 20 can no longer store any more oxygen. For this reason, after the time $t_2$, the output air-fuel ratio of the downstream side air-fuel ratio sensor 41 becomes leaner than the stoichiometric air-fuel ratio.

If, at the time $t_3$, fuel cut control is made to end, to make the upstream side exhaust purification catalyst 20 release the oxygen stored during fuel cut control, post reset rich control is performed. In the post reset rich control, an air-fuel ratio slightly richer than the stoichiometric air-fuel ratio is exhausted from the engine body 1. Along with this, the output air-fuel ratio of the upstream side air-fuel ratio sensor 40 becomes the rich air-fuel ratio and the oxygen storage amount of the upstream side exhaust purification catalyst 20 gradually decreases. At this time, even if rich air-fuel ratio exhaust gas is made to flow into the upstream side exhaust purification catalyst 20, the oxygen stored in the upstream side exhaust purification catalyst 20 and the unburned gas in the exhaust gas react, and therefore the air-fuel ratio of the exhaust gas exhausted from the upstream side exhaust purification catalyst 20 becomes substantially the stoichiometric air-fuel ratio. For this reason, the output air-fuel ratio of the downstream side air-fuel ratio sensor 41 becomes substantially the stoichiometric air-fuel ratio.

If the oxygen storage amount continues to decrease, finally the oxygen storage amount becomes substantially zero and unburned gas flows out from the upstream side exhaust purification catalyst 20. Due to this, at the time $t_4$, the exhaust air-fuel ratio detected by the downstream side air-fuel ratio sensor 41 becomes richer than the stoichiometric air-fuel ratio. If in this way the output air-fuel ratio of the downstream side air-fuel ratio sensor 41 reaches an end judgment air-fuel ratio slightly richer than the stoichiometric air-fuel ratio, the post reset rich control is made to end. After that, normal air-fuel ratio control is started. In the illustrated example, the air-fuel ratio of the exhaust gas exhausted from the engine body is controlled to become the stoichiometric air-fuel ratio.

Note that, the condition for ending post reset rich control need not necessarily be the time when the downstream side air-fuel ratio sensor 41 detects the rich air-fuel ratio. For example, the control may also be ended when a certain time period elapses after the end of fuel cut control or under other conditions.

<Problem in Diagnosis of Deterioration of Response>

As explained above, when setting the fuel injection amount based on the air-fuel ratio sensors 40, 41, if the air-fuel ratio sensors 40, 41 become abnormal and the precision of output of the air-fuel ratio sensors 40, 41 ends up deteriorating, it no longer becomes possible to optimally set the fuel injection amount. As a result, deterioration of the exhaust emissions and deterioration of the fuel economy end up being invited. For this reason, in many internal combustion engines, a diagnosis system is provided for self-diagnosing abnormality of the air-fuel ratio sensors 40, 41.

In this regard, as such an abnormality of output of the air-fuel ratio sensors 40, 41, deterioration of response may be mentioned. Deterioration of response of the air-fuel ratio sensor, for example, occurs due to air holes provided in a sensor cover (cover provided at outside from protective layer 55) for preventing a sensor element from being covered by water ending up being partially clogged by particulate matter (PM). The state of the trends in an air-fuel ratio sensor when such deterioration of response occurs is shown in FIG. 6.

Figure 6:
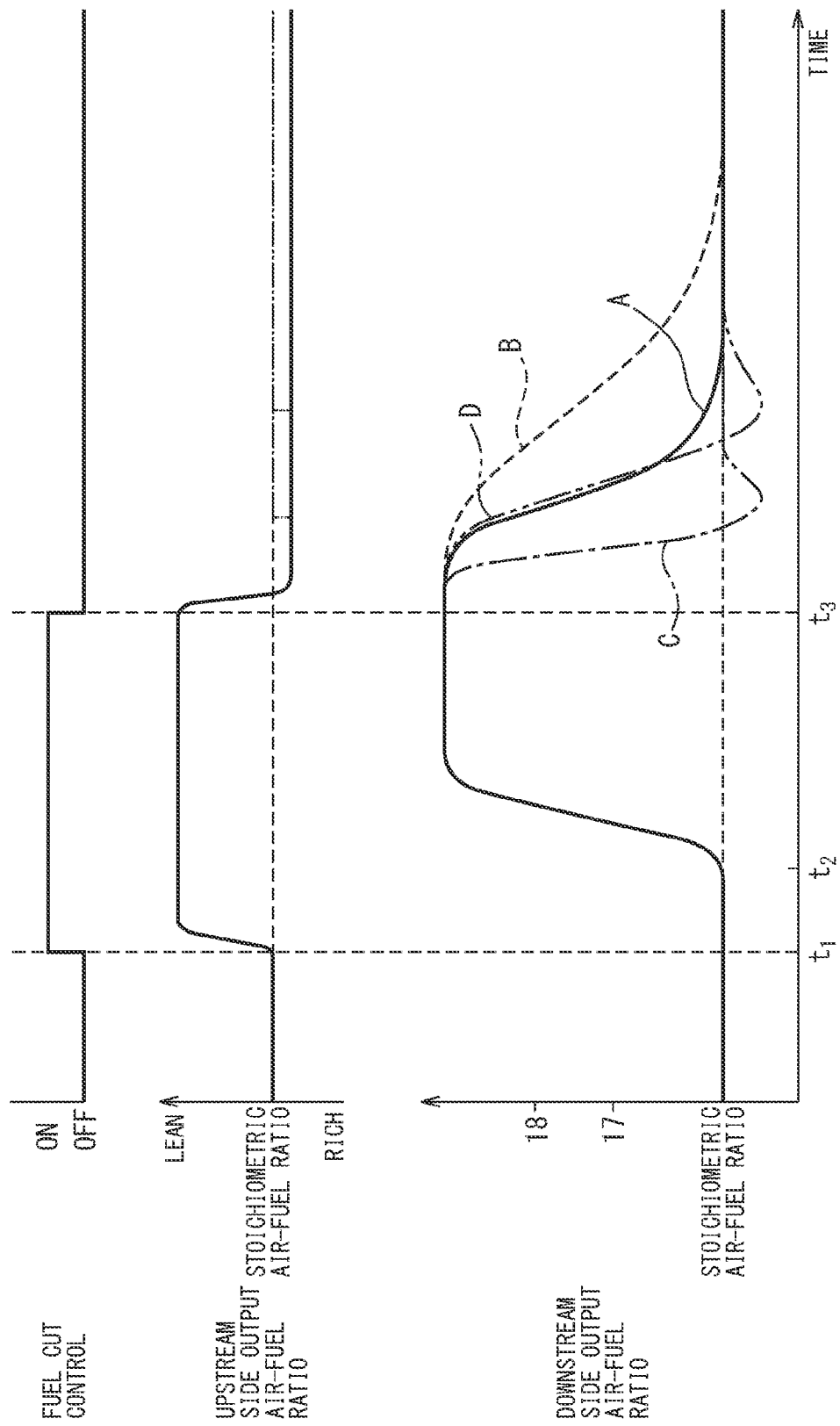
FIG. 6 is a time chart of an upstream side output air-fuel ratio, downstream side output air-fuel ratio, etc. before and after fuel cut control.

FIG. 6 is a time chart similar to FIG. 5 of the upstream side output air-fuel ratio and downstream side output air-fuel ratio before and after fuel cut control. In the illustrated example, fuel cut control is started at the time $t_1$ and fuel cut control is ended at the time $t_3$. If fuel cut control is ended, due to post reset rich control, rich air-fuel ratio exhaust gas is made to flow into the upstream side exhaust purification catalyst 20.

If the downstream side air-fuel ratio sensor 41 does not suffer from deterioration of response, the output air-fuel ratio of the downstream side air-fuel ratio sensor 41 follows a trend as shown in FIG. 6 by the solid line A. That is, after the end of fuel cut control, since there is distance between the engine body 1 to the downstream side air-fuel ratio sensor 41, the output air-fuel ratio of the downstream side air-fuel ratio sensor 41 starts to fall while delayed slightly from the end of fuel cut control. Further, at this time, the air-fuel ratio of the exhaust gas flowing out from the upstream side exhaust purification catalyst 20 becomes substantially the stoichiometric air-fuel ratio, and therefore the output air-fuel ratio of the downstream side air-fuel ratio sensor 41 also converges to substantially the stoichiometric air-fuel ratio.

On the other hand, if the downstream side air-fuel ratio sensor 41 suffers from the deterioration of response, the output air-fuel ratio of the downstream side air-fuel ratio sensor 41 follows a trend as shown in FIG. 6 by the broken line B. That is, compared with when the downstream side air-fuel ratio sensor 41 does not suffer from deterioration of response (solid line A), the speed of fall of the output air-fuel ratio becomes slower. In this way, the speed of fall of the output air-fuel ratio of the downstream side air-fuel ratio sensor 41 changes in accordance with any deterioration of response of the downstream side air-fuel ratio sensor 41. For this reason, by calculating this speed of fall, the presence of any deterioration of response of the downstream side air-fuel ratio sensor 41 can be diagnosed. In particular, such deterioration of response is preferably diagnosed based on the speed of fall in the region where the exhaust air-fuel ratio is between 18 or so and 17 or so.

In this regard, the trend in the output air-fuel ratio of the downstream side air-fuel ratio sensor 41 after the end of fuel cut control also changes according to the degree of deterioration of the upstream side exhaust purification catalyst 20. For example, if the degree of deterioration of the upstream side exhaust purification catalyst 20 is high and the oxygen storage ability falls, the upstream side exhaust purification catalyst 20 does not store almost any oxygen even during fuel cut control. For this reason, if fuel cut control ends and the air-fuel ratio of the exhaust gas flowing into the upstream side exhaust purification catalyst 20 is made the rich air-fuel ratio, along with this, the air-fuel ratio of the exhaust gas flowing out from the upstream side exhaust purification catalyst 20 also rapidly falls.

This state is shown in FIG. 6 by the one-dot chain line C. In FIG. 6, the one-dot chain line C expresses the trend in the output air-fuel ratio in the case where the downstream side air-fuel ratio sensor 41 does not suffer from deterioration of response and the degree of deterioration of the upstream side exhaust purification catalyst 20 is high. As will be understood from a comparison of the solid line A and one-dot chain line C of FIG. 6, after the end of fuel cut control, the speed of change of the output air-fuel ratio of the downstream side air-fuel ratio sensor 41 becomes faster than the case where the upstream side exhaust purification catalyst 20 has not deteriorated.

On the other hand, if the downstream side air-fuel ratio sensor 41 suffers from deterioration of response and the degree of deterioration of the upstream side exhaust purification catalyst 20 is high, the decrease in the speed of fall of the output air-fuel ratio accompanying deterioration of response and the increase in the speed of fall of the output air-fuel ratio accompanying deterioration of the upstream side exhaust purification catalyst 20 are matched. As a result, in such a case, the output air-fuel ratio of the downstream side air-fuel ratio sensor 41, as shown in FIG. 6 by the two-dot chain line D, follows the same trend as the output air-fuel ratio in the case of the solid line A (case where downstream side air-fuel ratio sensor 41 does not suffer from deterioration of response and degree of deterioration of the upstream side exhaust purification catalyst 20 is low) in the region of the exhaust air-fuel ratio between 18 or so and 17 or so.

For this reason, if, as explained above, the speed of fall of the output air-fuel ratio is used as the basis for diagnosing deterioration of response, as shown in FIG. 6 by the two-dot chain line D, it is not possible to judge abnormality regardless of the downstream side air-fuel ratio sensor 41 suffering from the abnormality of deterioration of response.

<Principle of Diagnosis of Abnormality in Present Invention>

As opposed to this, in an embodiment according to the present invention, in two different air-fuel ratio regions, the speeds of change of the output air-fuel ratio of the downstream side air-fuel ratio sensor 41 in those air-fuel ratio regions are calculated, and based on the calculated speeds of change at the air-fuel ratio regions, abnormality of the downstream side air-fuel ratio sensor 41 (in particular, deterioration of response) is diagnosed. Below, referring to FIG. 7 and FIG. 8, the principle of diagnosis of abnormality of the downstream side air-fuel ratio sensor 41 in the present invention will be explained.

As explained above, in the region between output air-fuel ratios of about 18 and about 17, so long as the degree of deterioration of the upstream side exhaust purification catalyst 20 is low, it is possible to detect the presence or absence of deterioration of response of the output air-fuel ratio of the downstream side air-fuel ratio sensor 41. Therefore, in the present embodiment, after the end of fuel cut control, the speed of change of the output air-fuel ratio when the output air-fuel ratio of the downstream side air-fuel ratio sensor 41 first passes through a first air-fuel ratio region X between 18 and 17 (see FIG. 7) (below, referred to as "the first change of speed of air-fuel ratio") is calculated. The time period $\Delta T_1$ from when changing from the upper limit air-fuel ratio of the first air-fuel ratio region (that is, 18) to the lower limit air-fuel ratio of the first air-fuel ratio region (that is, 17) is used as a parameter expressing the first change of speed of air-fuel ratio. The longer this first time period of change of the air-fuel ratio $\Delta T_1$, the slower the first change of speed of air-fuel ratio becomes. Note that, in FIG. 1, the first time period of change of the air-fuel ratio $\Delta T_1$ is a parameter showing the first change of speed of air-fuel ratio regarding the solid line A.

In addition, in the present embodiment, the speed of change of the output air-fuel ratio when the output air-fuel ratio of the downstream side air-fuel ratio sensor 41 is in a second air-fuel ratio region Y (see FIG. 7) between an air-fuel ratio slightly leaner than the stoichiometric air-fuel ratio (for example, 14.7) and an air-fuel ratio slight richer than the stoichiometric air-fuel ratio (for example, 14.5) (below, referred to as "second change of speed of air-fuel ratio") is calculated. Regarding this second change of speed of air-fuel ratio as well, in the same way as the first change of speed of air-fuel ratio, the time period $\Delta T_2$ from when changing from the upper limit air-fuel ratio of the second air-fuel ratio region to the lower limit air-fuel ratio of the second air-fuel ratio region is used as a parameter expressing the second change of speed of air-fuel ratio. The longer the second time period of change of the air-fuel ratio $\Delta T_2$ is, the slower the second change of speed of air-fuel ratio becomes. Note that, in FIG. 1, the second time period of change of the air-fuel ratio $\Delta T_2$ is a parameter showing the first change of speed of air-fuel ratio regarding the solid line A.

Here, the solid line A and the one-dot chain line C in the case where the downstream side air-fuel ratio sensor 41 does not suffer from the abnormality of deterioration of response will be compared. As a result, it is understood that in the one-dot chain line C of the case where the degree of deterioration of the upstream side exhaust purification catalyst 20 is high, the first change of speed of air-fuel ratio in the first air-fuel ratio region X is faster (first time period of change of air-fuel ratio $\Delta T_1$ is shorter) than the solid line A of the case where the degree of deterioration of the upstream side exhaust purification catalyst 20 is low. In addition, it is also understood that at the one-dot chain line C, the second change of speed of air-fuel ratio in the second air-fuel ratio region Y is faster (second time period of change of air-fuel ratio $\Delta T_2$ is shorter) compared with the solid line A.

Similarly, the broken line B and the two-dot chain line D in the case where the downstream side air-fuel ratio sensor 41 suffers from the abnormality of deterioration of response will be compared. As a result, it is understood that in the two-dot chain line D of the case where the degree of deterioration of the upstream side exhaust purification catalyst 20 is high, the first change of speed of air-fuel ratio in the first air-fuel ratio region X is faster (first time period of change of air-fuel ratio $\Delta T_1$ is shorter) than the broken line B of the case where the degree of deterioration of the upstream side exhaust purification catalyst 20 is low. In addition, it is also understood that at the two-dot chain line D, the second change of speed of air-fuel ratio in the second air-fuel ratio region Y is faster (second time period of change of air-fuel ratio $\Delta T_2$ is shorter) compared with the broken line B.

If combining these for judgment, it will be understood that the higher the degree of deterioration of the upstream side exhaust purification catalyst 20, the faster both the first change of speed of air-fuel ratio and the second change of speed of air-fuel ratio become. Considered conversely, it can be said that, the degree of deterioration of the upstream side exhaust purification catalyst 20 is understood based on the second change of speed of air-fuel ratio and that, based on this, the amount of change of the first change of speed of air-fuel ratio due to the degree of deterioration of the upstream side exhaust purification catalyst 20 is understood. Therefore, in the present embodiment, the second change of speed of air-fuel ratio is calculated and the first change of speed of air-fuel ratio is corrected based on the calculated second change of speed of air-fuel ratio.

Figure 8:
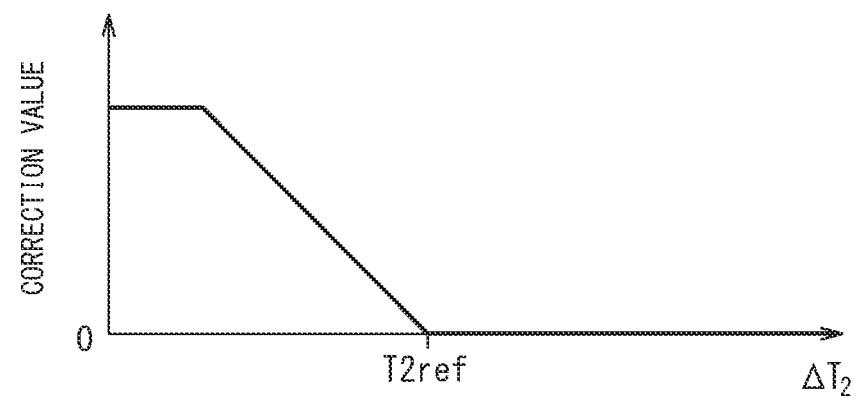
FIG. 8 is a view showing the relationship between a second time period of change of the air-fuel ratio and a correction value.

FIG. 8 is a view showing the relationship between the second time period of change of the air-fuel ratio $\Delta T_2$ and a correction value M. As will be understood from FIG. 8, the correction value M is a value which becomes smaller the longer the second time period of change of the air-fuel ratio $\Delta T_2$ (the slower the second change of speed of air-fuel ratio). That is, the longer the second time period of change of the air-fuel ratio $\Delta T_2$, the greater the amount of oxygen able to be stored by the upstream side exhaust purification catalyst 20 and therefore the smaller the degree of deterioration of the upstream side exhaust purification catalyst 20. For this reason, the longer the second time period of change of the air-fuel ratio $\Delta T_2$ is, the smaller the need to correct the first change of speed of air-fuel ratio. In particular, in the present embodiment, when the second time period of change of the air-fuel ratio $\Delta T_2$ becomes the reference time period T2ref or more, the correction value M is made zero. Therefore, according to the present embodiment, when the reference period of time T2ref or more elapses from when the output air-fuel ratio of the downstream side air-fuel ratio sensor 41 enters the second air-fuel ratio region Y, correction based on the second time period of change of the air-fuel ratio $\Delta T_2$ is not performed.

The thus calculated correction value M is added to the first time period of change of the air-fuel ratio $\Delta T_1$. What is thus calculated is made the corrected time period of change of the air-fuel ratio $\Delta T_{1M}(=\Delta T_1+M)$. Therefore, in the present embodiment, the first time period of change of the air-fuel ratio $\Delta T_1$ is corrected so that the shorter the second time period of change of the air-fuel ratio $\Delta T_2$, the longer the corrected time period of change of the air-fuel ratio $\Delta T_{1M}$ becomes. In other words, in the present embodiment, it can be said that the first change of speed of air-fuel ratio is corrected so that the faster the second change of speed of air-fuel ratio, the slower the corrected change of speed of air-fuel ratio becomes. As explained above, the first time period of change of the air-fuel ratio is affected by deterioration of response of the output air-fuel ratio of the downstream side air-fuel ratio sensor 41 and deterioration of the upstream side exhaust purification catalyst 20, but by correcting these in this way, it is possible to eliminate the effect of the degree of deterioration of the upstream side exhaust purification catalyst 20 from the first time period of change of the air-fuel ratio.

In the present embodiment, based on the thus calculated corrected time period of change of the air-fuel ratio $\Delta T_{1M}$, abnormality of the downstream side air-fuel ratio sensor 41 is diagnosed. Specifically, when the corrected time period of change of the air-fuel ratio $\Delta T_{1M}$ is longer than the time period of change used as reference for abnormality, that is, when the corrected change of speed of air-fuel ratio is slower than the speed of change used as reference for abnormality, it is judged that the downstream side air-fuel ratio sensor 41 suffers from the abnormality of deterioration of response.

Note that, the time period of change used as reference for abnormality is, for example, made a time period slightly longer than the minimum time period at which the time period of change can be obtained in the first air-fuel ratio region X when the downstream side air-fuel ratio sensor 41 does not suffer from deterioration of response and the degree of deterioration of the upstream side exhaust purification catalyst 20 is low. Further, the time period of change used as reference for abnormality may be a predetermined value or may be a value changing according to the engine speed or engine load or other operating parameter during post reset rich control.

Conversely, when the corrected time period of change of the air-fuel ratio $\Delta T_{1M}$ is shorter than the time period of change used as reference for abnormality, that is, when the corrected change of speed of air-fuel ratio is faster than the speed of change used as reference for abnormality, it is judged that the downstream side air-fuel ratio sensor 41 does not suffer from the abnormality of deterioration of response and the downstream side air-fuel ratio sensor 41 is normal. By diagnosing abnormality of the downstream side air-fuel ratio sensor 41 in this way, even if the upstream side exhaust purification catalyst 20 deteriorates, the downstream side air-fuel ratio sensor 41 can be accurately diagnosed for the abnormality of deterioration of response.

Note that, the calculation of the first change of speed of air-fuel ratio based on the output air-fuel ratio of the downstream side air-fuel ratio sensor 41 is performed by the first change speed calculating means, while the calculation of the second change of speed of air-fuel ratio based on the output air-fuel ratio of the downstream side air-fuel ratio sensor 41 is performed by the second change speed calculating means. Further, the judgment of normality and abnormality of the downstream side air-fuel ratio sensor 41 based on the first change of speed of air-fuel ratio and second change of speed of air-fuel ratio is performed by the abnormality diagnosing means. The ECU 31 functions as the first change speed calculating means, second change speed calculating means, and abnormality diagnosing means.

Further, in the present embodiment, when the diagnosis system judges that the downstream side air-fuel ratio sensor 41 is abnormal, a warning light is lit at the vehicle mounting the internal combustion engine.

In addition, as explained above, in the case of the one-dot chain line C and in the case of the two-dot chain line D, that is, when the second time period of change of the air-fuel ratio is short, the degree of deterioration of the upstream side exhaust purification catalyst 20 becomes high. Therefore, in these cases, it may be judged that the upstream side exhaust purification catalyst 20 is deteriorating. Specifically, when the second time period of change of the air-fuel ratio is shorter than a predetermined time period of change for judgment of catalyst abnormality, it is judged that the upstream side exhaust purification catalyst 20 is deteriorating. Note that, the time period of change for judgment of catalyst abnormality does not necessarily have to be a constant value. For example, it may also be a value which changes in accordance with the engine speed and the engine load or other operating parameters.

Furthermore, in the above embodiment, abnormality is diagnosed based on the first time period of change of the air-fuel ratio $\Delta T_1$ and the second time period of change of the air-fuel ratio $\Delta T_2$. However, as the parameter expressing the first change of speed of air-fuel ratio, instead of the first time period of change of the air-fuel ratio $\Delta T_1$, it is also possible to use a first change of speed of air-fuel ratio $V_1$ obtained by subtracting from the first region upper limit air-fuel ratio the first region lower limit air-fuel ratio and dividing that value by the first time period of change of the air-fuel ratio. Further, as the parameter expressing the second change of speed of air-fuel ratio, instead of the second time period of change of the air-fuel ratio $\Delta T_2$, it is also possible to use a second change of speed of air-fuel ratio $V_2$ obtained by subtracting from the second region upper limit air-fuel ratio the second region lower limit air-fuel ratio and dividing that value by the second time period of change of the air-fuel ratio.

Alternatively, instead of the time periods of change of the air-fuel ratio $\Delta T_1$ and $\Delta T_2$, it is also possible to use the cumulative value of amount of exhaust gas passing through the downstream side air-fuel ratio sensor 41 while the output air-fuel ratio changes from the upper limit air-fuel ratio to the lower limit air-fuel ratio in the corresponding air-fuel ratio region. That is, instead of the first time period of change of the air-fuel ratio $\Delta T_1$, it is also possible to use the cumulative value of amount of exhaust gas passing through the downstream side air-fuel ratio sensor 41 while the output air-fuel ratio changes from the upper limit air-fuel ratio to the lower limit air-fuel ratio in the first air-fuel ratio region. Further, instead of the second time period of change of the air-fuel ratio $\Delta T_2$, it is also possible to use the cumulative value of amount of exhaust gas passing through the downstream side air-fuel ratio sensor 41 while the output air-fuel ratio changes from the upper limit air-fuel ratio to the lower limit air-fuel ratio in the second air-fuel ratio region. This cumulative value of amount of exhaust gas may be estimated from the output value of the air flowmeter 39 or may be estimated from the engine load and engine speed.

Figure 9:
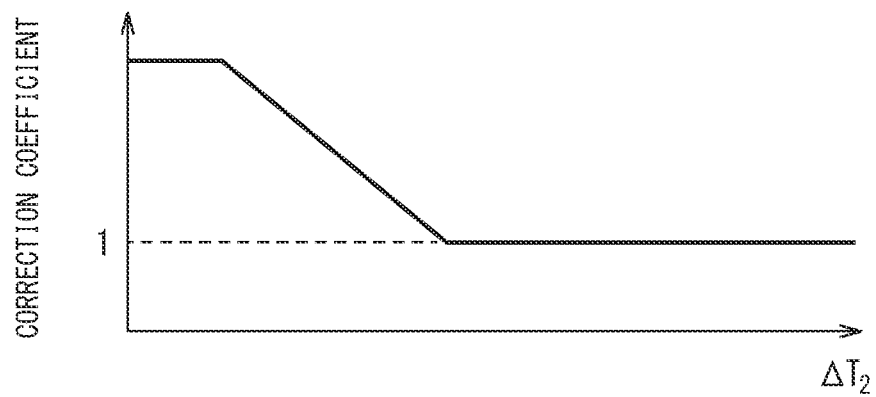
FIG. 9 is a view showing the relationship between a second time period of change of the air-fuel ratio and a correction coefficient.

In addition, in the above embodiment, the correction value M is calculated based on the second time period of change of the air-fuel ratio $\Delta T_2$ and this correction value M is added to the first time period of change of the air-fuel ratio $\Delta T_1$ of the air-fuel ratio to calculate the corrected time period of change of the air-fuel ratio $\Delta T_1$. However, it is also possible to calculate a correction coefficient K based on the second time period of change of the air-fuel ratio $\Delta T_2$ and to multiply this correction coefficient K with the first time period of change of the air-fuel ratio $\Delta T_1$ to calculate the corrected time period of change $\Delta T_{1M}$ of the air-fuel ratio. In this case, the relationship between the second time period of change of the air-fuel ratio $\Delta T_2$ and the correction coefficient K becomes as shown in FIG. 9.

<First Air-Fuel Ratio Region and Second Air-Fuel Ratio Region>

In this regard, if making the first air-fuel ratio region a region between the first region upper limit air-fuel ratio and the first region lower limit air-fuel ratio at the rich side from this, in the above-mentioned example, the first region upper limit air-fuel ratio is made 18 and the first region lower limit air-fuel ratio is made 17. Further, if making the second air-fuel ratio region a region between the second region upper limit air-fuel ratio and a second region lower limit air-fuel ratio at the rich side from this, in the above-mentioned example, the second region upper limit air-fuel ratio is made about 14.7 and the second region lower limit air-fuel ratio is made about 14.5. However, the first air-fuel ratio region and the second air-fuel ratio region do not necessarily have to be regions between these.

First, the first air-fuel ratio region will be explained. The first air-fuel ratio region basically has to be a region in which the speed of change of the output air-fuel ratio changes when the downstream side air-fuel ratio sensor 41 suffers from deterioration of response. Therefore, the first region upper limit air-fuel ratio has to be lower than the output air-fuel ratio when air is discharged from the upstream side exhaust purification catalyst 20.

In addition, when using as the downstream side air-fuel ratio sensor 41 a limit current type air-fuel ratio sensor as explained above, the first region upper limit air-fuel ratio has to be an air-fuel ratio at which the downstream side air-fuel ratio sensor 41 can generate a limit current. For example, in the example shown in FIG. 3, when the applied voltage at the downstream side air-fuel ratio sensor 41 is made 0.4V, if the exhaust air-fuel ratio is 18 or so, the limit current is output, but if exhaust air-fuel ratio becomes more than this, the limit current is not output. If in this way the limit current is no longer output, the precision of the output current with respect to the actual air-fuel ratio deteriorates, and therefore the precision of detection of the air-fuel ratio falls. Therefore, the first region upper limit air-fuel ratio is made an air-fuel ratio at which the downstream side air-fuel ratio sensor 41 can generate a limit current. At an air-fuel ratio sensor having the V-I characteristic shown in FIG. 3, it is made 18 or less.

Alternatively, if using as the downstream side air-fuel ratio sensor 41 a sensor configured so that the applied voltage is made larger as the output current increases, the first region upper limit air-fuel ratio may also be used as the upper limit lean air-fuel ratio at which limit current is generated when applying a voltage at which limit current is generated when detecting exhaust gas corresponding to the stoichiometric air-fuel ratio.

Further, the timing at which the air-fuel ratio of the exhaust gas flowing out from the upstream side exhaust purification catalyst 20 becomes the stoichiometric air-fuel ratio changes according to the amount of oxygen which can be stored by the upstream side exhaust purification catalyst 20 (maximum oxygen storage amount). Therefore, if setting the first region lower limit air-fuel ratio lower than the stoichiometric air-fuel ratio, even if the deterioration of response of the downstream side air-fuel ratio sensor 41 is of the same extent, the timing changes depending on the maximum oxygen storage amount of the upstream side exhaust purification catalyst 20. Therefore, the first region lower limit air-fuel ratio has to be the stoichiometric air-fuel ratio or more. In particular, the first region lower limit air-fuel ratio is preferably leaner than the stoichiometric air-fuel ratio.

In addition, when using the limit current type air-fuel ratio sensor as the downstream side air-fuel ratio sensor 41 in the above way, the first region lower limit air-fuel ratio also has to be an air-fuel ratio at which the downstream side air-fuel ratio sensor 41 can generate a limit current. Therefore, in an air-fuel ratio sensor having the V-I characteristic shown in FIG. 3, it is made 12 or more. Note that, considering the point that both the first region upper limit air-fuel ratio and the first region lower limit air-fuel ratio have to be air-fuel ratios at which the downstream side air-fuel ratio sensor 41 can generate the limit current, the first air-fuel ratio region can be said to be a region in the air-fuel ratio region where the downstream side air-fuel ratio sensor 41 generates a limit current.

Next, the second air-fuel ratio region will be explained. The second air-fuel ratio region basically has to be a region in which the speed of change of the output air-fuel ratio changes in accordance with the degree of deterioration of the upstream side exhaust purification catalyst 20 regardless of the presence or absence of deterioration of response of the downstream side air-fuel ratio sensor 41. As explained above, the output air-fuel ratio near the stoichiometric air-fuel ratio changes in accordance with the degree of deterioration of the upstream side exhaust purification catalyst 20, and therefore the second air-fuel ratio region preferably includes the stoichiometric air-fuel ratio.

Therefore, the second region upper limit air-fuel ratio has to be the stoichiometric air-fuel ratio or more (for example, 14.7, 17, etc.). Further, in the same way as the above-mentioned first region upper limit air-fuel ratio, it has to be lower than the output air-fuel ratio when the upstream side exhaust purification catalyst 20 discharges air. In addition, when using a limit current type air-fuel ratio sensor as the downstream side air-fuel ratio sensor 41, the second region air-fuel ratio has to be an air-fuel ratio at which the downstream side air-fuel ratio sensor 41 can generate a limit current. Furthermore, to prevent the second change of speed of air-fuel ratio from being affected by the change of speed of air-fuel ratio in the first air-fuel ratio region, the second region upper limit air-fuel ratio is preferably the first region lower limit air-fuel ratio or less or richer (lower) than the first region lower limit air-fuel ratio.

On the other hand, the second region lower limit air-fuel ratio is required to be the stoichiometric air-fuel ratio or less. Further, if the timing of end of the post reset rich control is made the time when the output air-fuel ratio of the downstream side air-fuel ratio sensor 41 reaches an end judgment air-fuel ratio richer than the stoichiometric air-fuel ratio, the end judgment air-fuel ratio may also be made the second region lower limit air-fuel ratio. In addition, when as explained above using a limit current type air-fuel ratio sensor as the downstream side air-fuel ratio sensor 41, the second air-fuel ratio region is also made a region in the air-fuel ratio region at which the downstream side air-fuel ratio sensor 41 generates a limit current.

Note that, if explaining the relationship between the first air-fuel ratio region and second air-fuel ratio region in brief, in the present embodiment, it can be said that the first air-fuel ratio region preferably includes an air-fuel ratio region leaner than the second air-fuel ratio region, while the second air-fuel ratio region preferably includes an air-fuel ratio region richer than the first air-fuel ratio region.

<Flow Chart>

Figure 10:
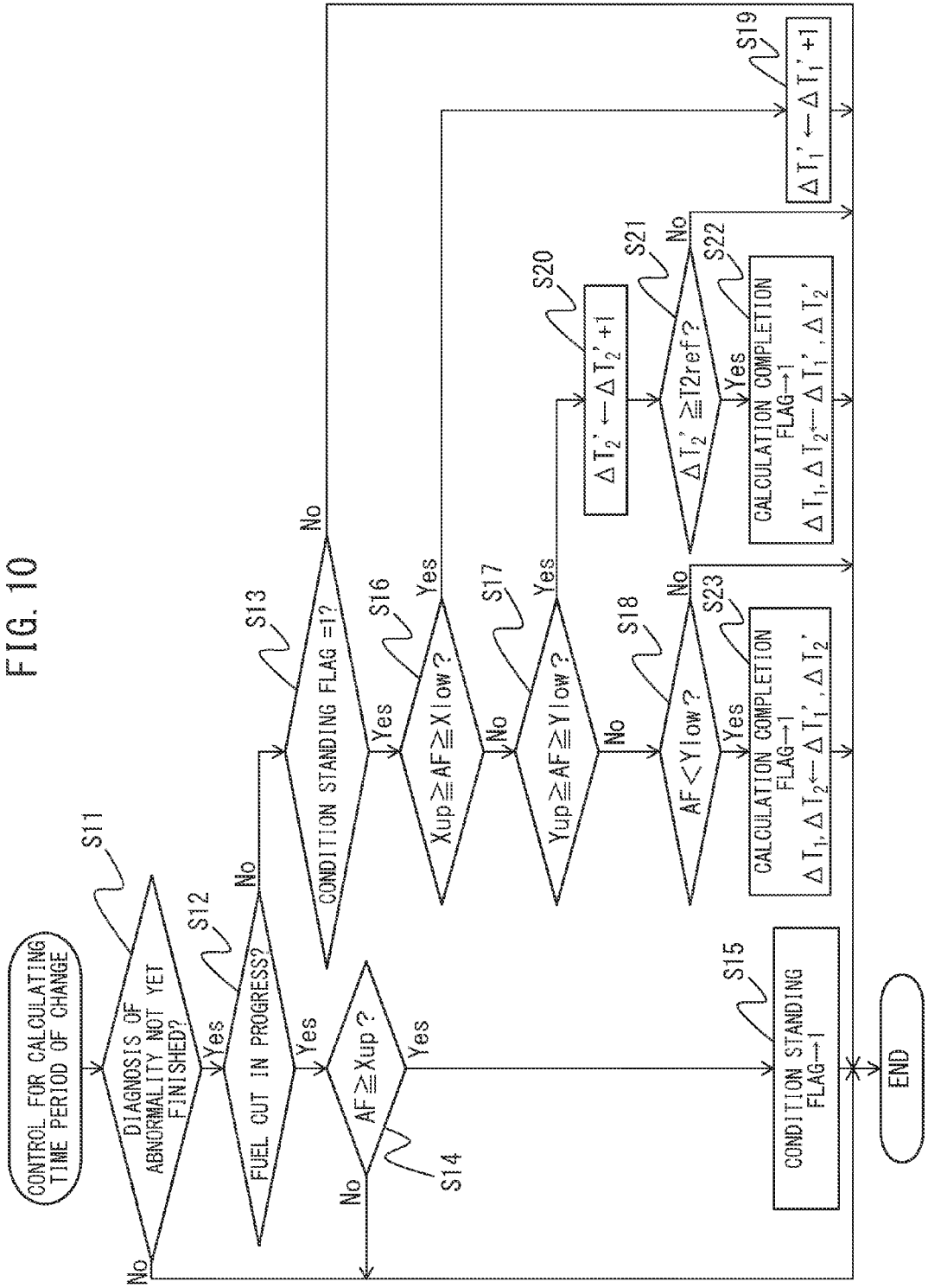
FIG. 10 is a flow chart which shows a control routine for control for calculating a time period of change.

FIG. 10 is a flow chart showing a control routine of control for calculating a time period of change. The illustrated control routine is performed by interruption every certain time interval.

First, at step S11, it is judged if diagnosis of abnormality has not already ended. When diagnosis of abnormality has already ended, there is no need to calculate the time period of change for diagnosing abnormality, and therefore the control routine is made to end. On the other hand, if at step S11 it is judged that the diagnosis of abnormality has not yet ended, the routine proceeds to step S12.

Next, at step S12, it is judged if fuel cut control is underway. When the fuel cut control is not being performed, the routine proceeds to step S13. At step S13, it is judged if the condition standing flag is "1". The condition standing flag is a flag made "1" when the condition of execution of calculation of the time period of change stands and made "0" when it does not stand. When the fuel cut control is still not being performed, the condition of execution of calculation of the time period of change does not stand, and therefore the control routine is made to end.

After that, if the fuel cut control is performed, the routine proceeds from step S12 to step S14. At step S14, it is judged if the output air-fuel ratio AF of the downstream side air-fuel ratio sensor 41 is the upper limit air-fuel ratio Xup of the first air-fuel ratio region X or more. If it is judged that the output air-fuel ratio AF of the downstream side air-fuel ratio sensor 41 is lower than the first region upper limit air-fuel ratio Xup, the time period of change at the first air-fuel ratio region X cannot be calculated, and therefore the control routine is made to end. On the other hand, if it is judged at step S14 that the output air-fuel ratio AF of the downstream side air-fuel ratio sensor 41 is the first region upper limit air-fuel ratio Xup or more, the routine proceeds to step S15. At step S15, the condition standing flag is made "1".

After that, if the fuel cut control is made to end, the routine proceeds from step S12 again to step S13. At step S13, it is judged that the condition standing flag is "1" and the routine proceeds to step S16 to calculate the time period of change. At steps S16 to S18, it is judged if the output air-fuel ratio AF of the downstream side air-fuel ratio sensor 41 is within the first air-fuel ratio region X (first region upper limit air-fuel ratio Xup to first region lower limit air-fuel ratio Xlow) (step S16), is within the second air-fuel ratio region Y (second region upper limit air-fuel ratio Yup to second region lower limit air-fuel ratio Ylow) (step S17), or has passed through both regions X and Y and become a value lower than the second region lower limit air-fuel ratio Ylow (step S18).

At steps S16 to S18, if it is judged that the output air-fuel ratio AF of the downstream side air-fuel ratio sensor 41 is within the first air-fuel ratio region X, the routine proceeds to step S19. At step S19, the provisional first time period of change $\Delta T_1'$ of the air-fuel ratio is incremented by "1". While the output air-fuel ratio AF of the downstream side air-fuel ratio sensor 41 is in the first air-fuel ratio region X, the routine repeatedly proceeds to step S19, and therefore during this, the provisional first time period of change $\Delta T_1'$ of the air-fuel ratio is increased. As a result, the time period during which the output air-fuel ratio AF is within the first air-fuel ratio region X is calculated.

Further, at steps S16 to S18, if it is judged that the output air-fuel ratio AF of the downstream side air-fuel ratio sensor 41 is within the second air-fuel ratio region Y, the routine proceeds to step S20. At step S20, the provisional second time period of change $\Delta T_2'$ of the air-fuel ratio is incremented by "1". While the output air-fuel ratio AF of the downstream side air-fuel ratio sensor 41 is in the second air-fuel ratio region Y, the routine repeatedly proceeds to step S20, and therefore during this period, the provisional second time period of change $\Delta T_1'$ of the air-fuel ratio increases. As a result, the time period during which the output air-fuel ratio AF is in the second air-fuel ratio region Y is calculated. Next, at step S21, it is judged if the provisional second time period of change $\Delta T_2'$ of the air-fuel ratio is the reference time period T2ref or more. When the provisional second time period of change $\Delta T_2'$ of the air-fuel ratio is smaller than the reference time period T2ref, the control routine is made to end and the increase of the provisional second time period of change $\Delta T_2'$ of the air-fuel ratio is repeated.

On the other hand, if at step S21 it is judged that the provisional second time period of change $\Delta T_2'$ of the air-fuel ratio is the reference time period T2ref or more, the provisional second time period of change $\Delta T_2'$ of the air-fuel ratio is no longer increased, and the correction value M calculated based on the time period $\Delta T_2$ will remain at zero without changing. For this reason, the calculation of the time period of change of the air-fuel ratio is completed, and the routine proceeds to step S22 where the calculation completion flag is set to "1". In addition, at step S22, the value of the provisional first time period of change of the air-fuel ratio $\Delta T_1$ and the value of the provisional second time period of change of the air-fuel ratio $\Delta T_2$ at this time are respectively made the first time period of change of the air-fuel ratio $\Delta T_1$ and the second time period of change of the air-fuel ratio $\Delta T_2$. Note that, the calculation completion flag is a flag made "0" until the time period $\Delta T_1$ and time period $\Delta T_2$ finish being calculated and made "1" when they finish being calculated.

On the other hand, if at step S16 to S18 it is judged that the output air-fuel ratio AF of the downstream side air-fuel ratio sensor 41 has passed through both the regions X and Y and become a value lower than the second region lower limit air-fuel ratio Ylow, the routine proceeds to step S23. At step S23, the time period of change of the air-fuel ratio has already finished being calculated, and therefore the calculation completion flag is set to "1". In addition, at step S23 as well, the value of the provisional first time period of change of the air-fuel ratio $\Delta T_1$ and the value of the provisional second time period of change of the air-fuel ratio $\Delta T_2$ at this time are respectively made the first time period of change of the air-fuel ratio $\Delta T_1$ and the second time period of change of the air-fuel ratio $\Delta T_2$.

Figure 11:
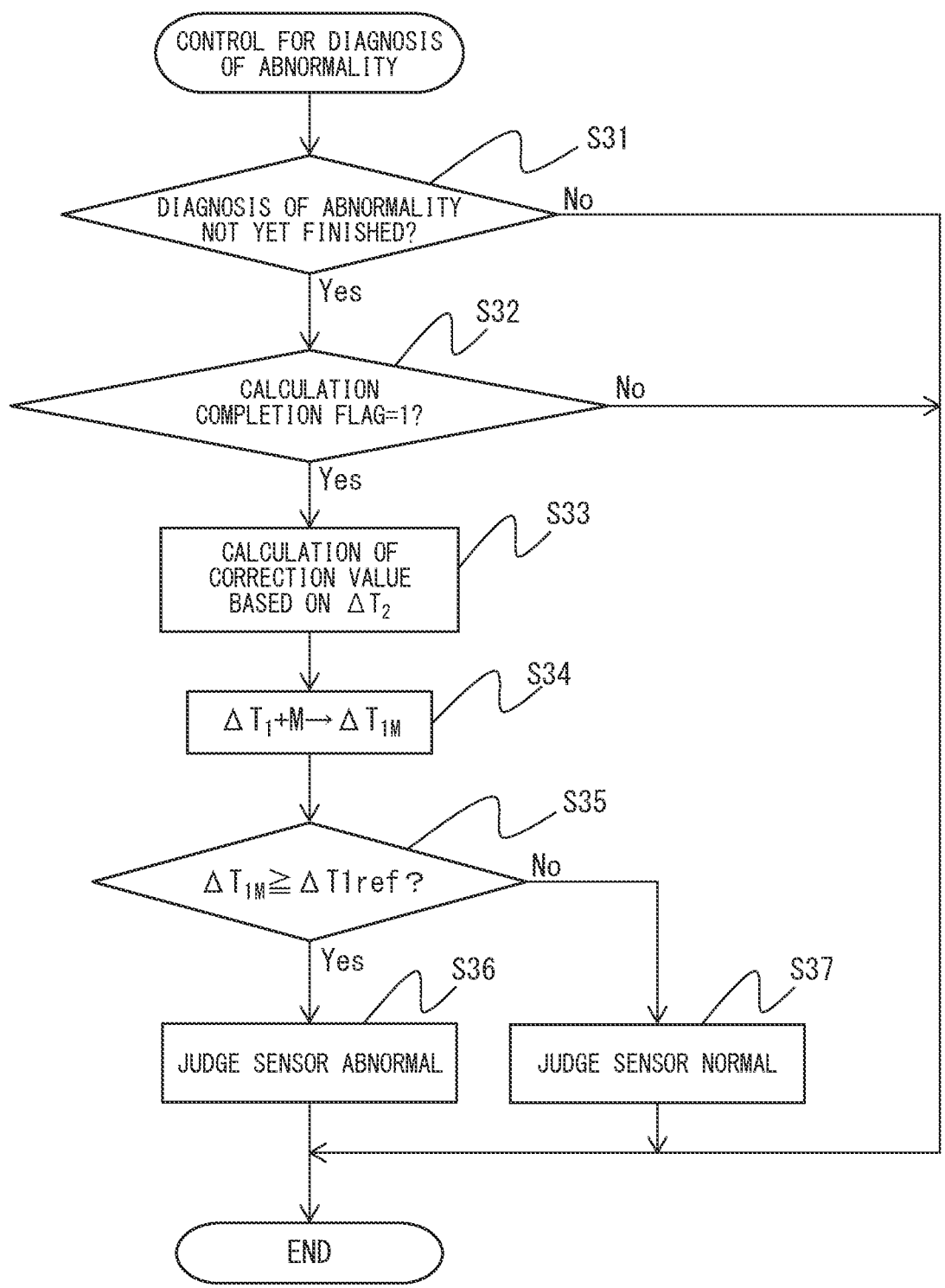
FIG. 11 is a flow chart which shows a control routine for control for diagnosing abnormality.

FIG. 11 is a flow chart showing a control routine of control for diagnosis of abnormality. The illustrated control routine is performed by interruption every certain time interval. In control for diagnosis of abnormality, the time period of change calculated by the control for calculation of the time period of change shown in FIG. 10 is utilized.

As shown in FIG. 11, first, at step S31, it is judged if diagnosis of abnormality has not yet ended. If the diagnosis of abnormality has already ended, it is not necessary to diagnose abnormality again, and therefore the control routine is made to end. On the other hand, if at step S31 it is judged that the diagnosis of abnormality has not yet ended, the routine proceeds to step S32.

At step S32, it is judged if the calculation completion flag is "1". Until the calculation completion flag is set to "1" by step S22 or S23 of FIG. 10, it is deemed that the calculation completion flag is not "1" and control routine is made to end. On the other hand, if the calculation completion flag is set to "1", the routine proceeds to step S33. At step S33, based on the time period of change $\Delta T_2$ calculated at step S22 or S24 of FIG. 10, the correction value M is calculated using a map such as shown in FIG. 8. Next, at step S34, the time period of change $\Delta T_1$ calculated at step S22 or S24 of FIG. 10 is increased by the correction value M calculated at step S33 to calculate the corrected time period of change of the air-fuel ratio $\Delta T_{1M}$.

Next, at step S35, it is judged if the corrected time period of change of the air-fuel ratio $\Delta T_{1M}$ is the time period of change used as reference for abnormality $\Delta T1ref$ or more. When it is judged that the corrected time period of change of the air-fuel ratio $\Delta T_{1M}$ is the time period of change used as reference for abnormality $\Delta T1ref$ or more, the routine proceeds to step S36 where it is judged that the downstream side air-fuel ratio sensor 41 suffers from the abnormality of deterioration of response. On the other hand, when it is judged that the corrected time period of change of the air-fuel ratio $\Delta T_{1M}$ is smaller than the time period of change used as reference for abnormality $\Delta T1ref$, the routine proceeds to step S37 where it is judged that the downstream side air-fuel ratio sensor 41 does not suffer from the abnormality of deterioration of response and is normal.

Note that, the condition standing flag and the calculation completion flag in the control routines shown in FIG. 10 and FIG. 11 are, for example, reset to zero when the ignition key of the vehicle mounting the internal combustion engine is turned off etc.

<Second Embodiment>

Next, referring to FIG. 12, a diagnosis system according to a second embodiment of the present invention will be explained. The diagnosis system according to the second embodiment basically is configured in the same way as the diagnosis system according to the first embodiment. However, in the first embodiment, only the speed of change (time period of change) of the output air-fuel ratio of the downstream side air-fuel ratio sensor 41 is used as the basis to diagnose abnormality, while in the second embodiment, a cumulative value (integrated value) of the output air-fuel ratio of the downstream side air-fuel ratio sensor 41 is also used as the basis to diagnose abnormality.

For the presence or absence of deterioration of response of the output air-fuel ratio of the downstream side air-fuel ratio sensor 41, the cumulative value of the output air-fuel ratio also exhibits a similar trend as the speed of change of the air-fuel ratio. This state is shown in FIG. 12.

Figure 7:
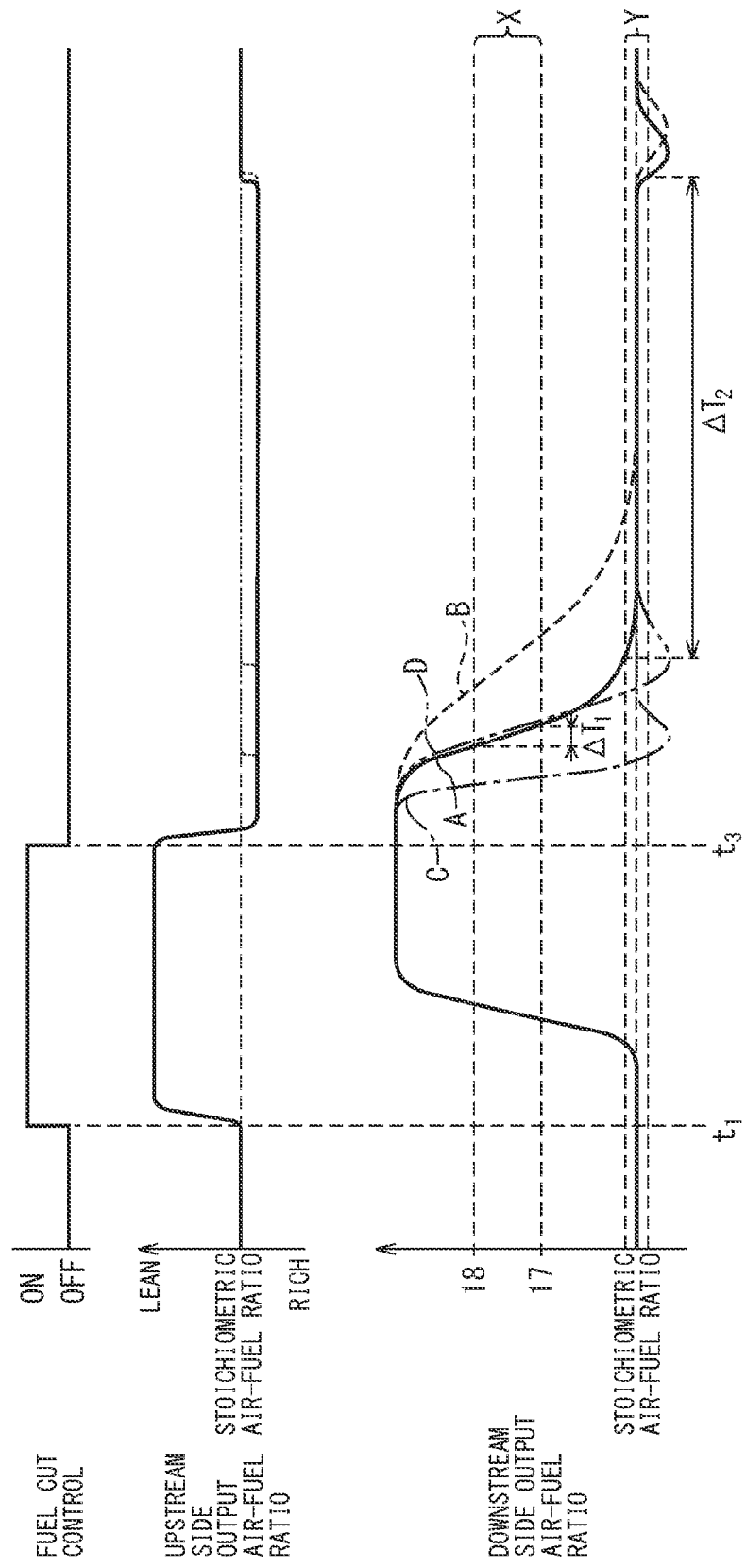
FIG. 7 is a time chart of an upstream side output air-fuel ratio, downstream side output air-fuel ratio, etc. before and after fuel cut control.
Figure 12:
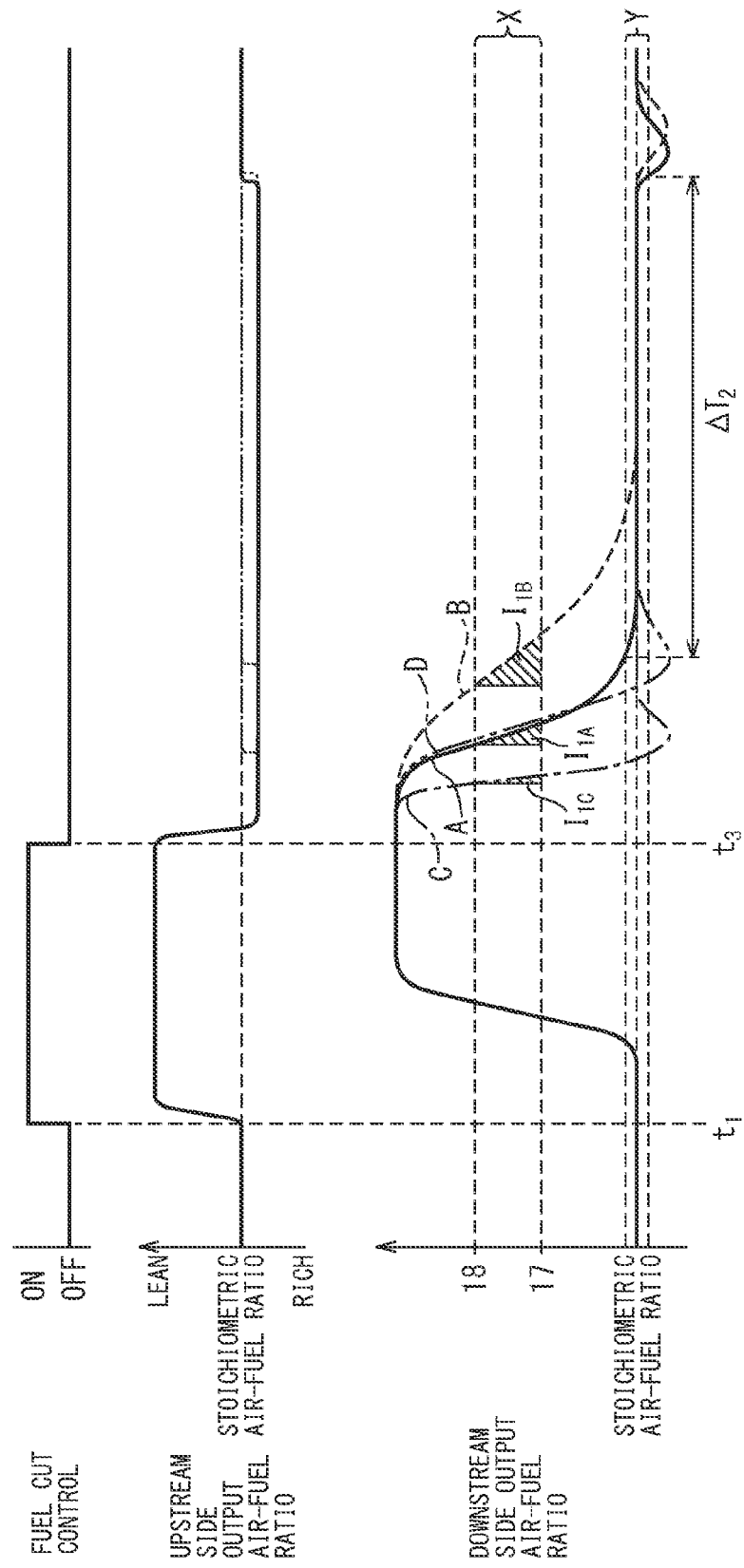
FIG. 12 is a time chart of an upstream side output air-fuel ratio and downstream side output air-fuel ratio etc. before and after fuel cut control.

FIG. 12 is a time chart similar to FIG. 7. In FIG. 12, $I_{1A}$ is the cumulative value of the output air-fuel ratio when the output air-fuel ratio first passes through the first air-fuel ratio region X in the case where the downstream side air-fuel ratio sensor 41 does not suffer from deterioration of response and the degree of deterioration of the upstream side exhaust purification catalyst 20 is low (solid line A). Further, in FIG. 12, $I_{1B}$ is the cumulative value of the output air-fuel ratio when the output air-fuel ratio first passes through the first air-fuel ratio region X in the case where the downstream side air-fuel ratio sensor 41 suffers from deterioration of response and the degree of deterioration of the upstream side exhaust purification catalyst 20 is low (solid line B). Furthermore, in FIG. 12, $I_{1C}$ is the cumulative value of the output air-fuel ratio when the output air-fuel ratio first passes through the first air-fuel ratio region X in the case where the downstream side air-fuel ratio sensor 41 does not suffer from deterioration of response and the degree of deterioration of the upstream side exhaust purification catalyst 20 is high (solid line C)

If comparing these cumulative values $I_{1A}$, $I_{1B}$, and $I_{1C}$, the cumulative value $I_{1B}$ is larger than the cumulative value $I_{1A}$.

Therefore, it is understood that if the downstream side air-fuel ratio sensor 41 suffers from deterioration of response, the cumulative value of the output air-fuel ratio when passing through the first air-fuel ratio region X becomes larger. Further, the cumulative value $I_{1C}$ is smaller than the cumulative value $I_{1A}$. Therefore, if the degree of deterioration of the upstream side exhaust purification catalyst 20 becomes higher, the cumulative value of the output air-fuel ratio when passing through the first air-fuel ratio region X becomes smaller.

On the other hand, when the downstream side air-fuel ratio sensor 41 does not suffer from deterioration of response and the degree of deterioration of the upstream side exhaust purification catalyst 20 is low (two-dot chain line D), the output air-fuel ratio exhibits behavior similar to the solid line A in the first air-fuel ratio region X. For this reason, in a case such as shown by the solid line A and in a case such as shown by the two-dot chain line D, the cumulative values of the output air-fuel ratios when the output air-fuel ratios first pass through the first air-fuel ratio region X (below, referred to as the "first cumulative value of air-fuel ratio") become the same extent.

In this way, it is understood that the first cumulative value of air-fuel ratio also exhibits a trend similar to the first change of speed of air-fuel ratio. Therefore, in the present embodiment, based on the first cumulative value of air-fuel ratio, abnormality of the downstream side air-fuel ratio sensor 41 is diagnosed. Specifically, in the same way as the first embodiment, the correction value calculated based on the second change of speed of air-fuel ratio (second time period of change of air-fuel ratio) is made the corrected cumulative value of air-fuel ratio in addition to the first cumulative value of air-fuel ratio. Further, when the corrected cumulative value of air-fuel ratio is the cumulative value used as reference for abnormality or more, it is judged that the downstream side air-fuel ratio sensor 41 suffers from the abnormality of deterioration of response. Conversely, when the corrected cumulative value of air-fuel ratio is smaller than the cumulative value used as reference for abnormality, it is judged that the downstream side air-fuel ratio sensor 41 does not suffer from the abnormality of deterioration of response.

Further, in the present embodiment, the first cumulative value of air-fuel ratio is corrected so that the shorter the second time period of change of the air-fuel ratio, the larger the corrected cumulative value of air-fuel ratio becomes. In other words, in the present embodiment, the first cumulative value of air-fuel ratio is corrected so that the faster the second change of speed of air-fuel ratio, the larger the corrected cumulative value of air-fuel ratio becomes. By diagnosing abnormality of the downstream side air-fuel ratio sensor 41 in this way, in the same way as the first embodiment, it is possible to accurately diagnose the abnormality of deterioration of response of the downstream side air-fuel ratio sensor 41 even if the upstream side exhaust purification catalyst 20 deteriorates.

<Third Embodiment>

Next, referring to FIG. 13, a diagnosis system according to a two embodiment of the present invention will be explained. The diagnosis system according to the third embodiment basically is configured in the same way as the diagnosis systems according to the first embodiment and second embodiment. However, in the first embodiment and second embodiment, the speed of change (time period of change) of the output air-fuel ratio of the downstream side air-fuel ratio sensor 41 when passing through the second air-fuel ratio region Y is used as the basis to diagnose abnormality, while in the third embodiment, the air-fuel ratio when the downstream side air-fuel ratio sensor 41 converges, defined as the converged output air-fuel ratio, is used as the basis to diagnose abnormality.

Figure 13:
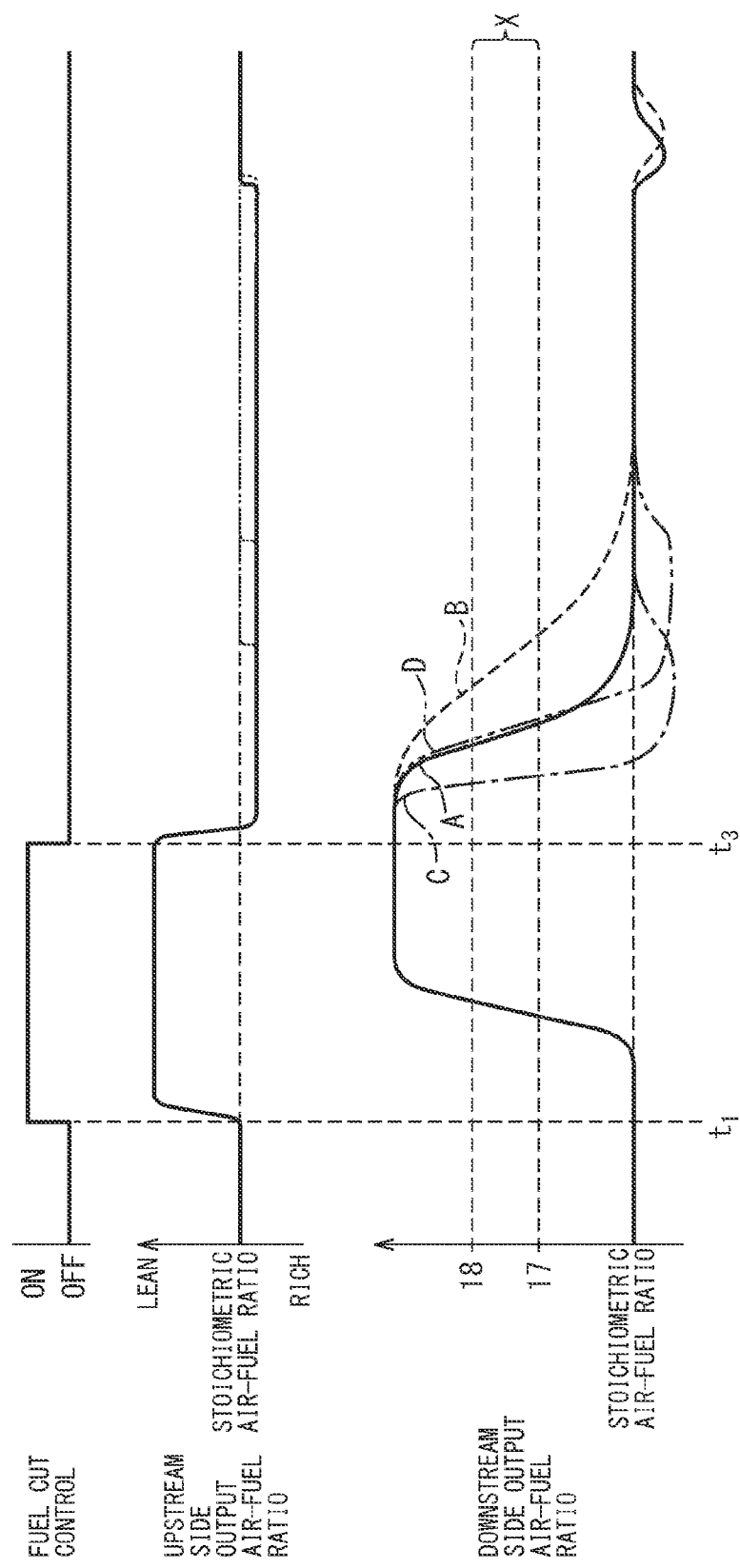
FIG. 13 is a time chart of an upstream side output air-fuel ratio and downstream side output air-fuel ratio etc. before and after fuel cut control.

FIG. 13 is a time chart similar to FIG. 7. However, in the example shown in FIG. 13, the post reset rich control is made to continue without being ended even if the output air-fuel ratio of the downstream side air-fuel ratio sensor 41 reaches the end judgment air-fuel ratio.

In FIG. 13, the solid line A and broken line B both show the case where the degree of deterioration of the upstream side exhaust purification catalyst 20 is low, but in this case, it is understood that the output air-fuel ratio of the downstream side air-fuel ratio sensor 41 converges to the stoichiometric air-fuel ratio. This is because when the degree of deterioration of the upstream side exhaust purification catalyst 20 is low, the upstream side exhaust purification catalyst 20 stores oxygen and that this stored oxygen is used to remove the unburned gas in the exhaust gas flowing into the upstream side exhaust purification catalyst 20.

On the other hand, the one-dot chain line C and two-dot chain line D in FIG. 13 both show cases where the degree of deterioration of the upstream side exhaust purification catalyst 20 is high. As will be understood from FIG. 13, in this case, the output air-fuel ratio of the downstream side air-fuel ratio sensor 41 converges to an air-fuel ratio richer than the stoichiometric air-fuel ratio, more accurately converges to an air-fuel ratio the same as the air-fuel ratio of the exhaust gas flowing into the upstream side exhaust purification catalyst 20. This is because if the degree of deterioration of the upstream side exhaust purification catalyst 20 is high, the upstream side exhaust purification catalyst 20 does not store almost any oxygen and as a result the exhaust gas flowing into the upstream side exhaust purification catalyst 20 flows out as is from the upstream side exhaust purification catalyst 20.

Considering such a phenomenon, in the present embodiment, the downstream side air-fuel ratio sensor 41 is diagnosed for abnormality as explained below. First, in the same way as the first embodiment or the second embodiment, the first time period of change of the air-fuel ratio $\Delta T_1$ is calculated. In addition, in the present embodiment, when diagnosing abnormality of the downstream side air-fuel ratio sensor 41, the post reset rich control is made to continue without ending it even when the output air-fuel ratio of the downstream side air-fuel ratio sensor 41 reached the end judgment air-fuel ratio. Further, the air-fuel ratio when the output air-fuel ratio of the downstream side air-fuel ratio sensor 41 first converges after the end of fuel cut control is calculated.

Figure 14:
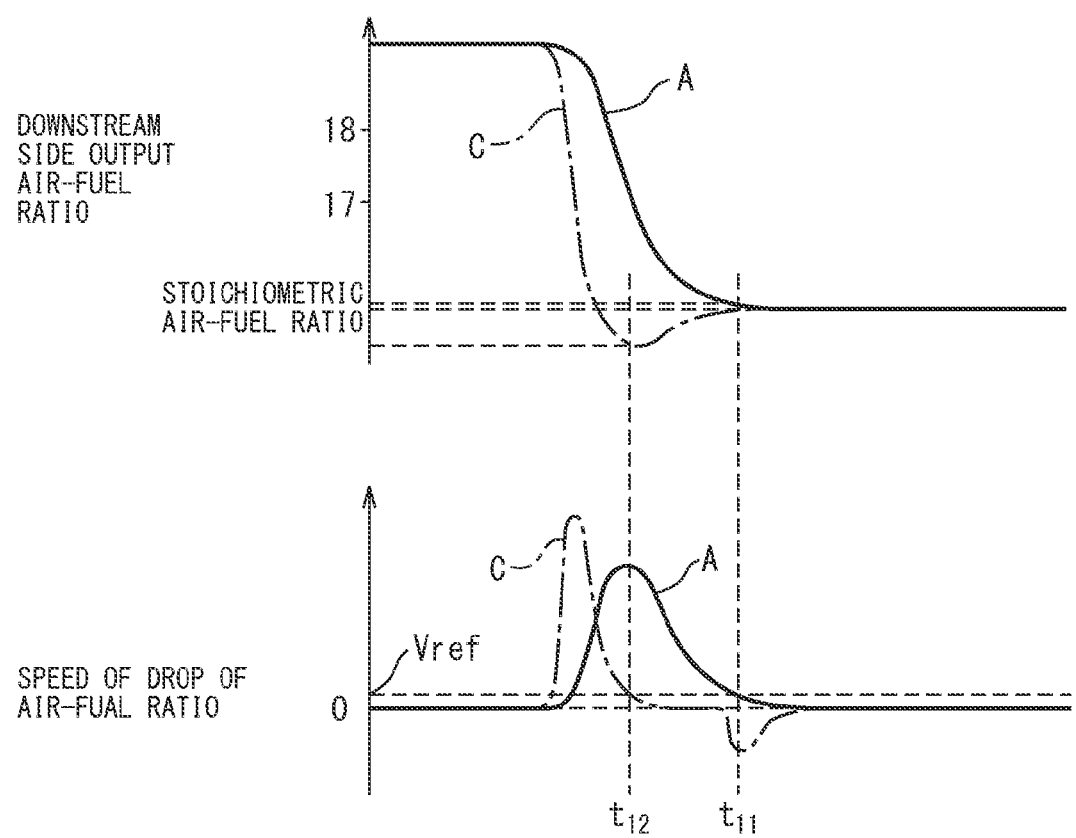
FIG. 14 is a time chart showing when the output air-fuel ratio of the downstream side air-fuel ratio sensor first converges.

FIG. 14 is a time chart showing when the output air-fuel ratio of the downstream side air-fuel ratio sensor 41 first converges. The trends in the output air-fuel ratio of the downstream side air-fuel ratio sensor 41 and its speed of drop are shown. In the figure, the solid line A shows the trend in the case where the downstream side air-fuel ratio sensor 41 does not suffer from deterioration of response and the degree of deterioration of the upstream side exhaust purification catalyst 20 is low. In the same way, the broken line C in the figure shows the trend when the downstream side air-fuel ratio sensor 41 does not suffer from deterioration of response and the degree of deterioration of the upstream side exhaust purification catalyst 20 is high.

In the present embodiment, the convergence of the output air-fuel ratio of the downstream side air-fuel ratio sensor 41 is judged based on the speed of fall of the output air-fuel ratio. In the example shown in FIG. 13, when the speed of fall of the output air-fuel ratio drops to a predetermined reference speed Vref or less, it is judged that the output air-fuel ratio of the downstream side air-fuel ratio sensor 41 has converged. Further, the output air-fuel ratio when it is judged that the output air-fuel ratio has converged in this way is made the output air-fuel ratio when the output air-fuel ratio of the downstream side air-fuel ratio sensor 41 first converges (below, referred to as "converged output air-fuel ratio"). Note that, the reference speed Vref is a value which changes in accordance with the engine speed, the engine load, or other operating parameters during the post reset rich control.

In the example shown in FIG. 14 by the solid line A, at the time $t_{11}$, it is judged that the output air-fuel ratio has converged and the output air-fuel ratio $\Delta F_{r11}$ at this time is made the converged output air-fuel ratio. In the present embodiment, if, in this way, the converged output air-fuel ratio of the time when the output air-fuel ratio of the downstream side air-fuel ratio sensor 41 first converges after the end of the fuel cut control is the stoichiometric air-fuel ratio or more, the degree of deterioration of the upstream side exhaust purification catalyst 20 is deemed low and the first change of speed of air-fuel ratio is not corrected.

On the other hand, in the example shown in FIG. 14 by the one-dot chain line C, at the time $t_{12}$, it is judged that the output air-fuel ratio has converged and the output air-fuel ratio $AF_{r12}$ at this time is made the output air-fuel ratio at the time of convergence. In the present embodiment, if, in this way, the converged output air-fuel ratio of the time when the output air-fuel ratio of the downstream side air-fuel ratio sensor 41 first converges after the end of fuel cut control is lower than the stoichiometric air-fuel ratio, the degree of deterioration of the upstream side exhaust purification catalyst 20 is deemed high and the first change of speed of air-fuel ratio is corrected. In particular, in the present embodiment, if the output air-fuel ratio of the downstream side air-fuel ratio sensor 41 converges to the rich air-fuel ratio, the correction value M is made a predetermined value.

Further, in the same way as the first embodiment, the thus calculated correction value M is used to correct the first change of speed of air-fuel ratio and calculate the corrected change of speed of air-fuel ratio, and based on this corrected change of speed of air-fuel ratio, abnormality of the downstream side air-fuel ratio sensor 41 is diagnosed. Specifically, in the same way as the first embodiment, the correction value M is added to the first time period of change of the air-fuel ratio $\Delta T_1$ and what is thus calculated is made the corrected time period of change of the air-fuel ratio $\Delta T_{1M}$ ($=\Delta T_1+M$).

According to the present embodiment, by diagnosing abnormality of the downstream side air-fuel ratio sensor 41 in this way, in the same way as the first embodiment and second embodiment, even if the upstream side exhaust purification catalyst 20 deteriorates, it is possible to accurately diagnose the abnormality of deterioration of response of the downstream side air-fuel ratio sensor 41.

Note that, in the above-mentioned way, in the present embodiment, when diagnosing abnormality of the downstream side air-fuel ratio sensor 41, the post reset rich control is continued without being ended even when the output air-fuel ratio of the downstream side air-fuel ratio sensor 41 reaches the end judgment air-fuel ratio. However, when not diagnosing abnormality of the downstream side air-fuel ratio sensor 41, the post reset rich control is made to end when the output air-fuel ratio of the downstream side air-fuel ratio sensor 41 reaches the end judgment air-fuel ratio.

In addition, in the present embodiment, when continuing the post reset rich control even after the output air-fuel ratio of the downstream side air-fuel ratio sensor 41 reaches the end judgment air-fuel ratio, the post reset rich control is made to end when it is judged that the output air-fuel ratio of the downstream side air-fuel ratio sensor 41 has converged (in the example shown in FIG. 13, the post reset rich control is made to end at the time $t_{12}$). Note that, the timing of end of the post reset rich control when diagnosing abnormality does not necessarily have to be when it is judged that the output air-fuel ratio has converged. For example, it may also be when the elapsed time from the time of start of post reset rich control, the total intake air amount, etc. reach preset predetermined values.

Further, in the present embodiment, instead of the first change of speed of air-fuel ratio (the first time period of change of the air-fuel ratio $\Delta T_1$), in the same way as the above second embodiment, the first cumulative value of air-fuel ratio may be used to diagnose the downstream side air-fuel ratio sensor 41.

In this case, the correction value calculated based on the converged output air-fuel ratio is made the corrected cumulative value of air-fuel ratio in addition to the first cumulative value of air-fuel ratio, and when this corrected cumulative value of air-fuel ratio is the cumulative value used as reference for abnormality or more, it is judged that the downstream side air-fuel ratio sensor 41 suffers from the abnormality of deterioration of response. Conversely, when the corrected cumulative value of air-fuel ratio is smaller than the cumulative value used as reference for abnormality, it is judged that the downstream side air-fuel ratio sensor 41 does not suffer from the abnormality of deterioration of response.

REFERENCE SIGNS LIST

1. engine body
5. combustion chamber
6. intake valve
8. exhaust valve
11. fuel injector
19. exhaust manifold
20. upstream side exhaust purification catalyst
21. upstream side casing
23. downstream side casing
24. downstream side exhaust purification catalyst
31. electronic control unit (ECU)
40. upstream side air-fuel ratio sensor
41. downstream side air-fuel ratio sensor

The invention claimed is:

1. A diagnosis system comprising: an internal combustion engine comprising an exhaust purification catalyst arranged in an exhaust passage of the internal combustion engine and able to store oxygen in inflowing exhaust gas and an air-fuel ratio sensor arranged at a downstream side of the exhaust purification catalyst in a direction of exhaust flow and detecting an air-fuel ratio of exhaust gas flowing out from the exhaust purification catalyst, stopping or decreasing a feed of fuel to a combustion chamber as fuel cut control, and controlling an air-fuel ratio of exhaust gas flowing into the exhaust purification catalyst after the end of the fuel cut control to a rich air-fuel ratio richer than a stoichiometric air-fuel ratio as post reset rich control, wherein the diagnosis system further comprises an electronic control unit that is configured to control an amount of fuel fed to the internal combustion engine based on output of the air-fuel ratio sensor, the electronic control unit further configured to calculate a first characteristic of change of air-fuel ratio when the output air-fuel ratio of the air-fuel ratio sensor first passes a first air-fuel ratio region which is a part of an air-fuel ratio region of a stoichiometric air-fuel ratio or more, after an end of the fuel cut control, based on an output air-fuel ratio output from the air-fuel ratio sensor, the electronic control unit is further configured to calculate a second characteristic of change of air-fuel ratio when the output air-fuel ratio of the air-fuel ratio sensor first passes a second air-fuel ratio region including the stoichiometric air-fuel ratio and different from the first air-fuel ratio region, after the end of the fuel cut control, based on an output air-fuel ratio output from the air-fuel ratio sensor, and the electronic control unit is further configured to diagnose abnormality of the air-fuel ratio sensor based on the first characteristic of change and the second characteristic of change calculated by the electronic control unit.

2. The abnormality diagnosis system of an internal combustion engine according to claim 1 wherein the electronic control unit is further configured to correct the first characteristic of change of air-fuel ratio based on the second characteristic of change of air-fuel ratio to calculate a corrected characteristic of change of air-fuel ratio and diagnoses abnormality of the air-fuel ratio sensor based on the corrected characteristic of change of air-fuel ratio.

3. The abnormality diagnosis system of an internal combustion engine according to claim 2 wherein the first characteristic of change of air-fuel ratio is a first change of speed of air-fuel ratio which is a speed of change when the output air-fuel ratio of the air-fuel ratio sensor first passes through the first air-fuel ratio region, and the electronic control unit is further configured to judge that the air-fuel ratio sensor is abnormal when a corrected change of speed of air-fuel ratio calculated by correcting the first change of speed of air-fuel ratio based on the second characteristic of change of air-fuel ratio is slower than a speed of change used as reference for abnormality, and to judge that the air-fuel ratio sensor is normal when the corrected change of speed of air-fuel ratio is faster than the speed of change used as reference for abnormality.

4. The abnormality diagnosis system of an internal combustion engine according to claim 3 wherein the second characteristic of change of air-fuel ratio is a second change of speed of air-fuel ratio which is a speed of change when an output air-fuel ratio of the air-fuel ratio sensor first passes through the second air-fuel ratio region, and the electronic control unit is further configured, in calculating the corrected change of speed of air-fuel ratio, to correct the first change of speed of air-fuel ratio so that the faster the second change of speed of air-fuel ratio, the slower the corrected change of speed of air-fuel ratio becomes.

5. The abnormality diagnosis system of an internal combustion engine according to claim 4 wherein the second air-fuel ratio region is a region between a second region upper limit air-fuel ratio leaner than the stoichiometric air-fuel ratio and a second region lower limit air-fuel ratio at a rich side from the stoichiometric air-fuel ratio.

6. The abnormality diagnosis system of an internal combustion engine according to claim 5 wherein the electronic control unit is further configured to not correct the first change of speed of air-fuel ratio or cumulative value of air-fuel ratio based on the second change of speed of air-fuel ratio when a predetermined time or more elapses from when an output air-fuel ratio of the air-fuel ratio sensor enters the second air-fuel ratio region.

7. The abnormality diagnosis system of an internal combustion engine according to claim 2 wherein
the first characteristic of change of air-fuel ratio is a first cumulative value of air-fuel ratio obtained by cumulatively adding the output air-fuel ratio of the air-fuel ratio sensor when the output air-fuel ratio is in the first air-fuel ratio region, and
the electronic control unit is further configured to judge that the air-fuel ratio sensor is abnormal when a corrected cumulative value of air-fuel ratio calculated by correcting the first cumulative value of air-fuel ratio based on the second characteristic of change of air-fuel ratio is a cumulative value used as reference for abnormality or more and judges that the air-fuel ratio sensor is normal when the corrected cumulative value of air-fuel ratio is smaller than the cumulative value used as reference for abnormality.

8. The abnormality diagnosis system of an internal combustion engine according to claim 7 wherein
the second characteristic of change of air-fuel ratio is a speed of change when an output air-fuel ratio of the air-fuel ratio sensor first passes through the second air-fuel ratio region, defined as a second change of speed of air-fuel ratio, and
the electronic control unit is further configured, in calculating the corrected cumulative value of air-fuel ratio, to correct the first cumulative value of air-fuel ratio so that the faster the second change of speed of air-fuel ratio, the slower the corrected cumulative value of air-fuel ratio becomes.

9. The abnormality diagnosis system of an internal combustion engine according to claim 1 wherein the air-fuel ratio sensor is a limit current type air-fuel ratio sensor outputting a limit current when an air-fuel ratio of exhaust gas passing through the air-fuel ratio sensor is within a predetermined air-fuel ratio region, and the first air-fuel ratio region and the second air-fuel ratio region are within the predetermined air-fuel ratio region where the air-fuel ratio sensor generates a limit current.

10. The abnormality diagnosis system of an internal combustion engine according to claim 1 wherein the first air-fuel ratio region is a region between the first region upper limit air-fuel ratio and a first region lower limit air-fuel ratio at a rich side from the first region upper limit air-fuel ratio, the second air-fuel ratio region is a region between the second region upper limit air-fuel ratio and a second region lower limit air-fuel ratio at a rich side from the second region upper limit air-fuel ratio, and the second region upper limit air-fuel ratio is the first region lower limit air-fuel ratio or less.

11. The abnormality diagnosis system of an internal combustion engine according to claim 1 wherein
the second characteristic of change of air-fuel ratio is a second change of speed of air-fuel ratio which is a change of speed when an output air-fuel ratio of the air-fuel ratio sensor first passes through the second air-fuel ratio region, and
the electronic control unit is further configured to judge that the exhaust purification catalyst is deteriorating when it is judged that the second change of speed of air-fuel ratio is faster than a speed of change of judgment of abnormality of catalyst.

12. The abnormality diagnosis system of an internal combustion engine according to claim 1, wherein in diagnosing abnormality of the air-fuel ratio sensor, when it is judged that the air-fuel ratio sensor is abnormal, a warning light is lit.

13. A diagnosis system comprising: an internal combustion engine comprising an exhaust purification catalyst arranged in an exhaust passage of the internal combustion engine and being able to store oxygen in inflowing exhaust gas and an air-fuel ratio sensor arranged at a downstream side of the exhaust purification catalyst in a direction of exhaust flow and detecting an air-fuel ratio of exhaust gas flowing out from the exhaust purification catalyst, stopping or decreasing a feed of fuel to a combustion chamber as fuel cut control, and controlling an air-fuel ratio of exhaust gas flowing into the exhaust purification catalyst after the end of the fuel cut control to a rich air-fuel ratio richer than a stoichiometric air-fuel ratio as post reset rich control,
wherein the diagnosis system further comprises
an electronic control unit that is configured to control an amount of fuel fed to the internal combustion engine based on output of the air-fuel ratio sensor;
the electronic control unit is configured to calculate a first change of speed of air-fuel ratio which is a change of speed when the output air-fuel ratio of the air-fuel ratio sensor first passes a first air-fuel ratio region which is a part of an air-fuel ratio region of a stoichiometric air-fuel ratio or more, after an end of the fuel cut control, based on an output air-fuel ratio output from the air-fuel ratio sensor,
the electronic control unit is further configured to calculate a second change of speed of air-fuel ratio which is a change of speed when the output air-fuel ratio of the air-fuel ratio sensor first passes a second air-fuel ratio region different from the first air-fuel ratio region, based on an output air-fuel ratio output from the air-fuel ratio sensor, and
the electronic control unit is further configured to diagnose abnormality of the air-fuel ratio sensor based on a corrected change of speed of air-fuel ratio calculated by correcting the calculated first change of speed of air-fuel ratio based on the calculated second change of speed of air-fuel ratio,
wherein the electronic control unit is further configured to correct the first change of speed of air-fuel ratio so that the corrected change of speed of air-fuel ratio becomes slower the faster the second change of speed of air-fuel ratio, to judge that the air-fuel ratio sensor is abnormal when the corrected change of speed of air-fuel ratio is slower than a speed of change used as reference for abnormality, and to judge that the air-fuel ratio sensor is normal when the first change of speed of air-fuel ratio corrected based on the second change of speed of air-fuel ratio is faster than a speed of change used as reference for abnormality.

* * * * *